(12) United States Patent
Yang et al.

(10) Patent No.: US 11,344,711 B2
(45) Date of Patent: May 31, 2022

(54) SWELLABLE ADHESIVE NEEDLES

(71) Applicant: The Brigham and Women's Hospital, Inc., Boston, MA (US)

(72) Inventors: Seung Yun Yang, Allston, MA (US); Jeffrey M. Karp, Brookline, MA (US); Eoin D. O'Cearbhaill, Cambridge, MA (US); Bohdan Pomahac, Dover, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 282 days.

(21) Appl. No.: 16/579,075

(22) Filed: Sep. 23, 2019

(65) Prior Publication Data

US 2020/0086101 A1    Mar. 19, 2020

Related U.S. Application Data

(63) Continuation of application No. 14/761,504, filed as application No. PCT/US2014/014105 on Jan. 31, 2014, now Pat. No. 10,420,922.

(Continued)

(51) Int. Cl.
*A61M 37/00*   (2006.01)
*A61B 17/064*   (2006.01)
(Continued)

(52) U.S. Cl.
CPC ....... *A61M 37/0015* (2013.01); *A61B 17/064* (2013.01); *A61B 17/08* (2013.01);
(Continued)

(58) Field of Classification Search
CPC .. A61M 37/0015; A61B 17/064; A61B 17/08; B29D 22/00; B32B 37/142; B32B 37/18; B32B 38/0012; Y10T 156/1043
(Continued)

(56) References Cited

U.S. PATENT DOCUMENTS 5,824,079 A    10/1998  Siegler et al.
5,985,355 A *  11/1999  Walther ................ A61L 31/10
                                                     427/2.28

(Continued)

FOREIGN PATENT DOCUMENTS

WO    WO 2009/094394    7/2009
WO    WO 2012/100002    7/2012

OTHER PUBLICATIONS

Donnelly et al., "Hydrogel-Forming Microneedle Arrays for Enhanced Transdermal Drug Delivery," Adv. Funct. Mater, 2012, 22: 4879-4890.

(Continued)

*Primary Examiner* — Phillip A Gray
(74) *Attorney, Agent, or Firm* — Fish & Richardson P.C.

(57) ABSTRACT

This disclosure relates to swellable needles that include a proximal end portion and a swellable distal end portion. Upon exposure to a liquid, the needles are configured to undergo a shape change from a first configuration in which the width of the needle is tapered from the proximal end portion to the distal end portion to a second configuration in which the distal end portion is more swollen than the proximal end portion. The swellable needles can be double layer swellable needles or single material swellable needles.

26 Claims, 24 Drawing Sheets

Related U.S. Application Data

(60) Provisional application No. 61/759,901, filed on Feb. 1, 2013.

(51) Int. Cl.
*B29D 22/00* (2006.01)
*B32B 37/18* (2006.01)
*B32B 37/14* (2006.01)
*B32B 38/00* (2006.01)
*A61B 17/08* (2006.01)
*A61B 17/00* (2006.01)
*A61B 17/06* (2006.01)

(52) U.S. Cl.
CPC ........... *B29D 22/00* (2013.01); *B32B 37/142* (2013.01); *B32B 37/18* (2013.01); *B32B 38/0012* (2013.01); *A61B 2017/00893* (2013.01); *A61B 2017/00898* (2013.01); *A61B 2017/0641* (2013.01); *A61B 2017/06176* (2013.01); *A61M 2037/0023* (2013.01); *A61M 2037/0046* (2013.01); *A61M 2037/0053* (2013.01); *A61M 2037/0061* (2013.01); *B32B 2535/00* (2013.01); *Y10T 156/1043* (2015.01)

(58) Field of Classification Search
USPC .......................................................... 604/46
See application file for complete search history.

(56) References Cited

U.S. PATENT DOCUMENTS

| | | |
|---|---|---|
| 2010/0256064 A1 | 10/2010 | Woolfson et al. |
| 2010/0305603 A1 | 12/2010 | Nielsen et al. |
| 2011/0195124 A1 | 8/2011 | Jin |
| 2014/0114277 A1 | 4/2014 | Eggert |

OTHER PUBLICATIONS

International Preliminary Report on Patentability in International Application No. PCT/US2014/014105, dated Aug. 4, 2015, 9 pages.
International Search Report and Written Opinion in International Application No. PCT/US2014/014105, dated May 20, 2014, 13 pages.

* cited by examiner

SWELLABLE ADHESIVE NEEDLES

CLAIM OF PRIORITY

This application is a continuation of U.S. patent application Ser. No. 14/761,504, filed Jul. 16, 2015, which is a U.S. National Phase Application under 35 U.S.C. § 371 of International Patent Application No. PCT/US2014/014105, filed on Jan. 31, 2014, which claims priority to U.S. Provisional Application Ser. No. 61/759,901, filed on Feb. 1, 2013, the entire contents of all of which are hereby incorporated by reference.

STATEMENT AS TO FEDERALLY SPONSORED RESEARCH

This invention was made with Government support under Grant No. GM086433 awarded by the National Institutes of Health. The Government has certain rights in the invention.

FIELD OF THE INVENTION

The invention relates to swellable adhesive needles and needle adhesives, e.g., swellable microneedle adhesives.

BACKGROUND OF THE INVENTION

There are many approaches to achieving adhesion with soft tissues. Chemical adhesives, such as cyanoacrylate, adhere strongly to tissues by a reactive exothermic covalent cross-linking reaction. Fibrin glues and biocompatible hydrogel adhesives covalently bond to some tissues. Sutures and surgical staples based on mechanical fixation are also widely used.

SUMMARY OF THE INVENTION

The invention is based, at least in part, on the discovery that needle adhesives, e.g., formed as a single swellable needle or as an array of swellable needles, e.g., microneedles, can be applied to a substrate that contains a liquid or moisture, e.g., tissue of a person or animal, with a low penetration force, provide high levels of adhesion to the tissue, and can be removed without significant damage to the tissue. The needles forming a needle adhesive are rigid and conical in their dry state and thus can easily penetrate tissue. Upon insertion into tissue, a swollen bulb is formed at the end of each needle. These bulbs locally displace the surrounding tissue as they swell, mechanically interlocking with the tissue and causing the needle adhesive to adhere strongly to the tissue. Upon removal from the tissue, the needles can, in some implementations, return to their dry, non-swollen state. In some examples, the swellable needles are double layer swellable needles, in which each needle includes a swellable outer layer that swells as it absorbs liquid from the tissue. In some examples, the swellable needles are formed of a single material. We use the term "swellable needles" to refer generally to double layer swellable needles and single material swellable needles.

In one general aspect, double layer swellable needles include an inner core formed of a first material; and an outer layer coating at least a distal end portion of the core and formed of a second material different than the first material. The outer layer is configured to swell upon insertion of the needle into a substrate comprising a liquid.

Various implementations of these double layer swellable needles can include one or more of the following features. The outer layer can be configured to swell preferentially at a distal end of the needle. Swelling of the outer layer causes the needle to adhere to the substrate. An insertion force to insert the needle into the substrate can be less than a removal force to remove the needle from the substrate after swelling has occurred. A thickness of the outer layer at the distal end of the needle can be at least about 20% of an overall length of the needle. In some cases, the thickness of the outer layer at the distal end of the needle can be at least about 40% of the overall length of the needle. An adhesion force of the needle to the substrate depends on a ratio of a thickness of the swollen outer layer at the distal end of the needle to an overall length of the needle.

When the outer layer is not swollen, the width of the needle can be tapered from a proximal end to a distal end.

The inner core can be formed of a non-swellable material. The inner core can be formed of polystyrene. The outer layer can be formed of a block copolymer. For example, the outer layer can be formed of polystyrene-block-poly(acrylic acid) (PS-b-PAA).

In some implementations, the stiffness of the outer layer can decrease upon swelling of the outer layer. The swelling of the outer layer can be reversible upon removal of the needle from the substrate. The inner core and the outer layer can be interlocked via entanglement of polymer chains. The needles can include a drug reservoir for holding a drug, wherein the drug is released into the substrate upon swelling of the outer layer. In some cases, the outer layer is the drug reservoir. In some implementations, the substrate is a biological tissue, e.g., of a human or animal, either living or dead.

In another general aspect, swellable needles include a proximal end portion and a swellable distal end portion. Upon exposure to a liquid, the needles are configured to undergo a shape change from a first configuration in which the width of the needle is tapered from the proximal end portion to the distal end portion to a second configuration in which the distal end portion is more swollen than the proximal end portion.

Various embodiments of these swellable needles can include one or more of the following features. The needles can be configured to be inserted into a substrate, and wherein an adhesion force of the needle to the substrate is higher in the second configuration than in the first configuration. In some cases, the adhesion force of the needles to the substrate is at least about five times higher in the second configuration than in the first configuration. In some embodiments, the adhesion force of the needle to the substrate depends on a ratio of a thickness of the swollen distal end portion to an overall length of the needle.

In some implementations, an insertion force to insert the needle into a substrate is less than a removal force to remove the needle from the substrate. In some cases, the substrate is a biological tissue. The needles can be configured to reversibly undergo a shape change between the first configuration and the second configuration. The needles can be configured to undergo the shape change to the second configuration upon insertion into a substrate. The needles can be configured to undergo a return shape change from the second configuration to the first configuration upon exposure to a dry environment.

In some implementations, a stiffness of the distal end portion is higher when the needle is in the first configuration than when the needle is in the second configuration. In the second configuration, an outer layer of the needle is swollen and the shape of an inner core of the needle remains substantially unchanged.

In another general aspect, double layer swellable needle arrays include a backing and a plurality of double layer swellable needles arranged on the backing. Each needle in the array includes an inner core formed of a first material; and an outer layer coating at least a distal end portion of the core and formed of a second material different than the first material. The outer layer is configured to swell upon insertion of the needle into a substrate comprising a liquid.

Various implementations of these double layer swellable needle arrays can include one or more of the following features. For example, swelling of the outer layer of each needle can cause the needle array to adhere to the substrate. In some embodiments, an insertion force to insert the plurality of needles into the substrate is less than a removal force to remove the needle array from the substrate after swelling. The backing can be formed of a flexible material. The backing can include fluid drainage holes. In some embodiments, the backing is formed of a gas-permeable and liquid-impermeable material.

The needle arrays can include a drug reservoir for holding a drug, and wherein the drug is released into the substrate upon swelling of the outer layer. In some cases, the outer layer is the drug reservoir.

In another general aspect, methods for making a double layer swellable needle include forming an outer layer of the needle by coating a conical mold with a first material configured to swell upon exposure to a fluid. The first material is disposed at least at a distal tip portion of the conical mold. The method includes forming an inner core of the needle by filling the conical mold with a second material different than the first material. The method also includes removing the needle from the mold, whereby the outer layer is bound to the inner core.

Various implementations of these methods can include one or more of the following features. Coating the conical mold with the first material can include applying a solution of the first material to the mold; and allowing the solution to dry. Filling the conical mold with the second material can include melting the second material. In some embodiments, forming the inner core includes causing the first material and the second material to interlock via entanglement of polymer chains.

In some implementations, the second material is a non-swellable material. For example, the second material can be or include polystyrene. The first material can be or include a block copolymer. In some implementations, the first material can be or include polystyrene-block-poly(acrylic acid) (PS-b-PAA). The methods also can include loading the outer layer of the needle with a drug.

In another general aspect, methods for securing a material to a substrate include securing the material to the substrate with a swellable needle array including a plurality of needles. The securing includes inserting the plurality of needles into the substrate and allowing each of the plurality of needles to undergo a shape change from a first configuration to a second configuration. An adhesion force of the needle array to the substrate is higher when the needles are in the second configuration than when the needles are in the first configuration.

Various implementations of these methods can include one or more of the following features. For example, the adhesion force of the needle array to the substrate can be at least about five times higher in the second configuration than in the first configuration. Allowing each of the plurality of needles to undergo a shape change can include allowing a distal end portion of each needle to swell. Allowing each of the plurality of needles to undergo a shape change can include allowing the needle array to interlock with the substrate over a period of time, such as ten minutes. In the first configuration, the width of each needle can be tapered from a proximal end portion of the needle to a distal end portion of the needle. In the second configuration, the width of a distal end portion of each needle can be larger than the width of a proximal end portion of the needle. In some embodiments, allowing each of the plurality of needles to undergo a shape change can include allowing each needle to absorb a liquid.

The methods include removing the needle array from the substrate, wherein each of the plurality of needles undergoes a shape change from the second configuration to the first configuration upon removal of the needle array from the substrate. In some implementations, the substrate is a biological tissue. In some implementations, the material is a skin graft.

As used herein, the term "adhesion" refers to a tendency of two surfaces to cling together.

The needle adhesives described herein have a number of advantages. For instance, needle adhesives formed of micrometer-scale needles can provide strong tissue adhesion in normal and shear directions and are removable with minimal tissue damage, reducing the potential for infection and scarring. Adhesion can be achieved by mechanical interlocking between the swellable needles and the tissue without the need for additional adhesive material on the needles. Adhesion can be maintained to dry and wet tissue and to dynamic tissue surfaces. Needle adhesives can be applied quickly and are simple to position over a target site. Mechanical interaction with the target tissue reduces the possibility of an inflammatory response to the adhesive and provides intimate contact between the adhesive and the tissue that helps reduce the risk of infection. In addition, swellable needles can be used therapeutically to deliver agents such as antibacterial agents, pro-regenerative agents, anti-inflammatory agents, and/or analgesic agents to target tissues.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Needle adhesives formed from a single swellable needle or arrays of swellable needles can be applied to tissue with a low penetration force, provide high levels of adhesion to the tissue, and can be removed without significant damage to the tissue. The swellable needles forming a needle adhesive are rigid and conical in their dry state and thus can penetrate tissue. Upon insertion into tissue, a swollen bulb is formed at the end of each needle. These bulbs locally displace the surrounding tissue, mechanically interlocking with the tissue and causing the needle adhesive to adhere strongly to the tissue. Upon removal from the tissue, the swellable needles can return to their dry, non-swollen state. In some examples, the swellable needles are double layer swellable needles, each needle including a swellable outer layer that swells as it absorbs liquid from the tissue. In some examples, the swellable needles are formed of a single material. We use the term "swellable needles" to refer generally to double layer swellable needles and single material swellable needles.

Structure and Composition of Swellable Needles

Figure 1:
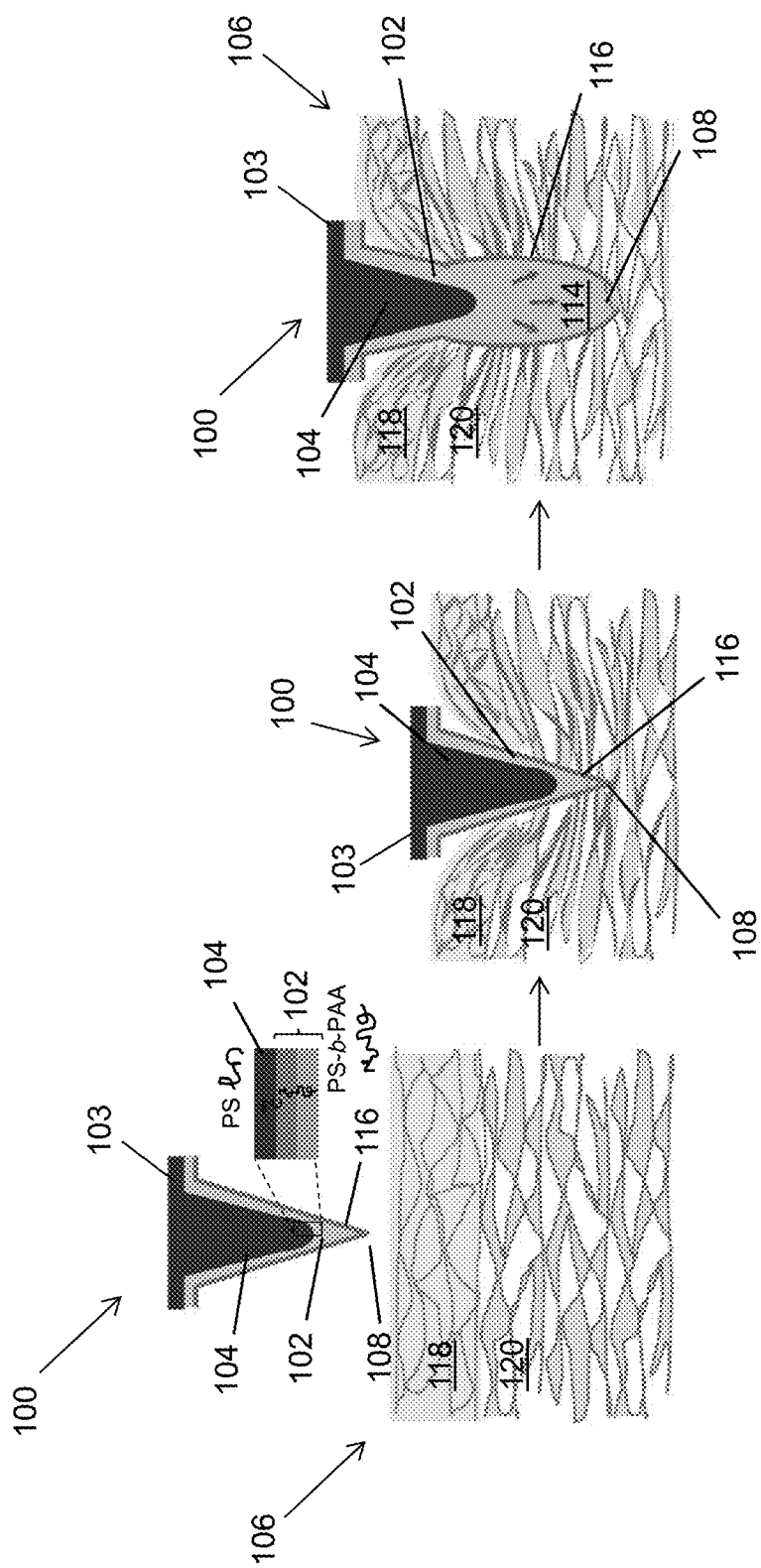
FIGS. 1A, 1B, and 1C are diagrams of a double layer swellable needle prior to, during, and after penetration into skin, respectively.

Referring to FIGS. 1A-1C, a double layer swellable needle 100 includes an outer layer 102 and an inner core 104. The double layer swellable needle 100 is attached to a backing 103. The outer layer 102 is formed of a material that swells upon contact with a liquid, such as an aqueous liquid or an organic liquid. The core 104 is formed of a material that does not swell upon contact with that same liquid.

In a dry (i.e., non-swollen) state (FIG. 1A), the double layer swellable needle 100 is tapered to a point at a distal tip 108, enabling the double layer swellable needle 100 to easily penetrate tissue 106, e.g., biological tissue such as skin, muscle, or organ tissue. Upon insertion into the tissue 106 (FIG. 1B), the double layer swellable needle 100 comes into contact with liquid in the tissue, such as blood or extracellular fluid, causing the outer layer 102 to swell. In a swollen state (FIG. 1C), the outer layer 102 of the double layer swellable needle is swollen and soft (i.e., with a lower modulus than in the dry state) while the core remains substantially unchanged.

The outer layer 102 can be thicker at the distal tip 108 than along the tapered sides of the double layer swellable needle 100. This selective localization of material of the outer layer 102 at the distal tip 108 of the double layer swellable needle causes swelling to occur preferentially at the distal tip 108. Thus, the outer layer 102 at the distal tip 108 swells down and to the sides, forming a bulb 114.

The bulb 114 locally deforms the tissue 106, mechanically interlocking with the tissue and anchoring the double layer swellable needle 100 in place. In this swollen state, the double layer swellable needle 100 exhibits high levels of adhesion with the tissue 106. Removal of the swollen needle 100 from the tissue can be performed without significant damage to the tissue and without fracture or delamination of the double layer swellable needle 100 due to the deformability (low modulus) of the swollen tip and the strong interfacial interaction between the swollen outer layer 102 and the core 104.

The materials of the outer layer 102 and the core 104 are swellable and non-swellable, respectively, upon exposure to a liquid. The materials of the outer layer 102 and the core 104 can also have mechanical and/or chemical interactions to prevent delamination between the outer layer 102 and the core 104.

In some implementations, the outer layer 102 can be formed of an amphiphilic block copolymer that exhibits selective responsiveness to stimuli such as the presence of aqueous or organic liquids. Block copolymers containing two or more polymer components (referred to herein as "blocks") connected by covalent bonds offer a way to combine characteristics of the individual polymer components into a hybrid material. For instance, the dual hydrophilic-hydrophobic properties of an amphiphilic block copolymer can enable rapid absorption of water by the outer layer 102 and promote interaction with a core 104 formed of a non-swellable, hydrophobic material. The mechanical properties and swellability of the outer layer 102 can be controlled by manipulating the overall average molecular weight of the polymer and the weight fraction of each block.

One example of a block copolymer that can be used to form the outer layer 102 is polystyrene-block-poly(acrylic acid) (PS-b-PAA). PAA is a super-absorbent polymer material that possesses carboxylic acid (COOH) groups that quickly become ionized in the presence of water. On the other hand, PS exhibits mechanical strength and structural integrity without swelling. The degree of swelling of the PS-b-PAA outer layer 102 can be increased by increasing the weight fraction of the PAA block. The mechanical robustness of the outer layer 102 can be strengthened by increasing the weight fraction of the PS block. In some cases, the PS block preferentially assembles into a thin PS layer 116 on the outer surface of the double layer swellable needle 100 (i.e., at the interface between the outer layer 102 and the air). The molecular weight of the PS block can affect the degree (e.g., the speed) of penetration of water through the PS layer 116 into the PS-b-PAA outer layer 102 and thus the kinetics of swelling of the outer layer 102. For instance, the short chains of a PS block with a relatively low molecular weight (e.g., less than about 100 kg mol$^{-1}$) provide low surface coverage of the outer layer-air interface, thus permitting rapid water penetration and thus enabling rapid swelling of the outer layer.

In one implementation, the number average molecular weight ($M_n$) of PS-b-PAA used for the outer layer 102 was 26 kg mol$^{-1}$ for PS and 76 kg mol$^{-1}$ for PAA, with a PS weight fraction of about 25%. This PS-b-PAA composition has a compressive modulus of about 0.23 MPa at a maximum swollen state, which approximates the stiffness of skin and intestine tissue. This similarity in stiffness can reduce the risk of tissue damage when the double layer swellable needle 100 is removed from that tissue. Other examples of compositions of PS-b-PAA can also be used. In general, the weight fraction of PS in the PS-b-PAA outer layer 102 can be any weight fraction that allows a substantially continuous PAA microstructure to form in the outer layer 102, thus enabling the outer layer 102 to absorb water and increase in volume after swelling. For instance, PS-b-PAA with a PS weight fraction between about 5% and about 70% can be used for adhesion with biological tissue.

Other examples of materials that can be used to form the outer layer 102 include, e.g., any polymer composition which can penetrate the tissue and which swells in the presence of liquid (e.g., an aqueous liquid, such as water, or a solvent). For instance, the outer layer can be formed of a homopolymer or blend of crosslinked polymers including one or more hydrophilic functional groups. Examples of suitable polymers include, but are not limited to, alginate, gelatin, collagen, dextran, chitosan, poly(vinyl alcohol), amylopectin, carboxymethylcellulose (CMC), poly(hydroxyethylmethacrylate) (polyHEMA), poly (acrylic acid), and poly(caprolactone), or a Gantrez®-type polymer. Gantrez®-type polymers include poly(methylvinylether/maleic acid), esters thereof, and similar, related, polymers (eg. poly(methyl/vinyl ether/maleic anhydride). The outer layer 102 can also be formed of a water-absorbing polymers can prepared by using a copolymer including at least one hydrophilic moiety. For instance, a grafting copolymer or a copolymer including one or more or a block copolymer, a random copolymer, or a regular alternating copolymer monomer sequence can be used. A hydrogel prepared using a polyionic dendrimer or polymer can also be used to form the outer layer 102.

The polymer composition of the outer layer 102 can be cross-linked, e.g., using any suitable cross-linking technique. The cross-linking can be physical, chemical, electrostatic, thermal, or a combination of those. Suitable cross-linking agents include polyhydric alcohols (e.g., glycerol, propylene glycol, poly(ethylene glycol)) or a polyamino compound (e.g., a compound that can form amide bonds with reactive groups of a polymer). Metal ions could be used as a cross-linking agent.

The core 104 can be formed of a rigid material or a flexible material. For a rigid core 104, a stiff, non-swellable material, such as PS homopolymer with a molecular weight between about 5 kg mol$^{-1}$ and about 1,000 kg mol$^{-1}$, can be used. For a flexible core 104, a flexible thermoplastic elastomer, such as styrene-isoprene-styrene, can be used. Examples of suitable polymers for stiff core material include, but are not necessarily limited to, Polylactic Acide (PLA), Polyglycolic Acid (PGA), poly(lactic-co-glycolic acid) (PLGA), Cellulose, Gelatin, Aliginate, Dextran, Sodium Carboxymethyl Cellulose (SCMC), Hydroxyethyl cellulose (HEC), Hydroxypropyl cellulose (HPC), hydroxypropyl methylcellulose (HPMC), Amylopectin (AMP), Hyaluronic acid, silicone, Polyvinylpyrolidone (PVP), Polyvinyl alcohol (PVA), Poly(vinylpyrrolidone-co-methacrylic acid) (PVA-MAA), Polyhydroxyethylmethacrylate (pHMEA), Polyethlene glycol (PEG), Polyethylen oxide (PEO), chrondroitin sulfate, dextrin, dextran, maltodextrin, chitin, chitosan, mono and polysaccharides, galactose, maltose, Poly(methyl methacrylate) (PMMA), Polyacrylonitrile (PAN), Polyethylene terephthalate (PET), Polyethylene (PE), Polypropylene (PP), Styrene-acrylonitrile (SAN). The stiff core 104 can be also formed by those prepolymer (or monomer) after crosslinking or in situ polymerization. For a flexible core 104, a flexible thermoplastic elastomer, such as styrene-isoprene-styrene, can be used. Examples of suitable polymers for soft core material include, but are not necessarily limited to, poly(glycerol sebacate) (PGS), poly(glycerol sebacate)-acrylate (PGSA), poly(citric diol), star-poly (s-caprolactone-co-D,L-lactide), poly(tri-methylene carbonate-co-s-caprolactone) and poly (tri-methylene carbonate-co-D,L-lactide), polyurethane (PU), thermoplastic copolyester, thermoplastic polyamides, and comercially available Arnitel (DSM), Engage (Dow Chemical), Hytrel (Du Pont), Dryflex and Mediprene (ELASTO), Kraton (Shell). The soft core 104 can be also formed by the prepolymer (or monomer) of elastomer after crosslinking or in situ polymerization.

The core 104 can be formed of a material that has a high level of adhesion with the material of the outer layer 102 in order to prevent delamination of the double layer swellable needle 100 when removed from the tissue 106. Strong adhesion between the PS-b-PAA outer layer 102 and the PS core 104 can be provided by hydrophobic interactions and chain entanglement between the PS block in the outer layer 102 and the PS core 104. In some examples, the molecular weight of the PS core 104 can be limited (e.g., to less than about 1000 kg mol$^{-1}$) in order to encourage entanglement between the outer layer 102 and the core 104.

Swellable needles 100 can be on a micrometer scale or millimeter scale, e.g., for tissue adhesion applications. Swellable needles 100 can also be on a centimeter scale or meter scale, e.g., for construction or industrial application.

The dimensions of a swellable needle 100 include the length L from the distal tip 108 to the intersection of the swellable needle 100 with the backing 103, the base diameter of the swellable needle 100 at its intersection with the backing 103, and the tip diameter at the distal tip 108 of the swellable needle. These dimensions and other dimensions can be selected, e.g., based on characteristics of the tissue or other material into which they are to be inserted, characteristics of an intended application of the swellable needles, or other considerations. For instance, at typical needle insertion sites into skin, the thickness of the epidermis 118 is less than about 100 µm and the depth from the skin surface to the nerve is about 1.2-1.7 mm. Swellable needles for insertion at these skin sites can be sized such that the swollen bulb 114 is entirely in the dermis 120 (i.e., below the epidermis 118) but does not contact the nerve. For instance, the length L of such a swellable needle can be about 700 µm. Longer or shorter swellable needles can also be fabricated. For instance, swellable needles for insertion into organ tissue can be about 5 mm in length. Swellable needles for non-biomedical applications, such as for applications in the construction industry can be, e.g., up to about 5 m or longer in length.

The base diameter of the swellable needles can be determined based on the mechanical strength (e.g., fracture force) of the swellable needles and the insertion force of the swellable needles, the latter of which is related to the contact area between the surface of the swellable needle and the tissue during insertion. The base diameter can be selected such that the swellable needles are not prone to breakage. For instance, for a PS-b-PAA based swellable needle that is 700 µm long, with a tip diameter of 10 µm, and with a modulus of about 1.5 GPa, the base diameter can be between about 100 µm and about 500 µm (e.g., about 280 µm) in order for the swellable needle to penetrate tissue without breaking. The tip diameter can be selected to allow the swellable needles to easily penetrate tissue and to achieve sufficient mechanical interlocking with the tissue. For instance, the tip diameter can be about 10 µm. In some examples, the tip diameter can be as small as possible and can be limited, e.g., by the resolution of the lithography and/or masking processes involved in fabricating the swellable needle.

In some examples, the length of the swellable needle and/or the tip diameter are selected to reduce or minimize pain related to swellable needle insertion. For instance, insertion of swellable needles less than about 700 µm long can be relatively painless, while insertion of longer swellable needles can cause pain. In some examples, the materials and/or dimensions of a swellable needle 100 are selected for a particular application, e.g., based on a cell composition, water content, tissue density, or another characteristic of a target tissue. For instance, the adhesion of a swellable needle to a specific type of tissue can be optimized by tailoring the materials and/or dimensions of the swellable needles.

Figure 2:
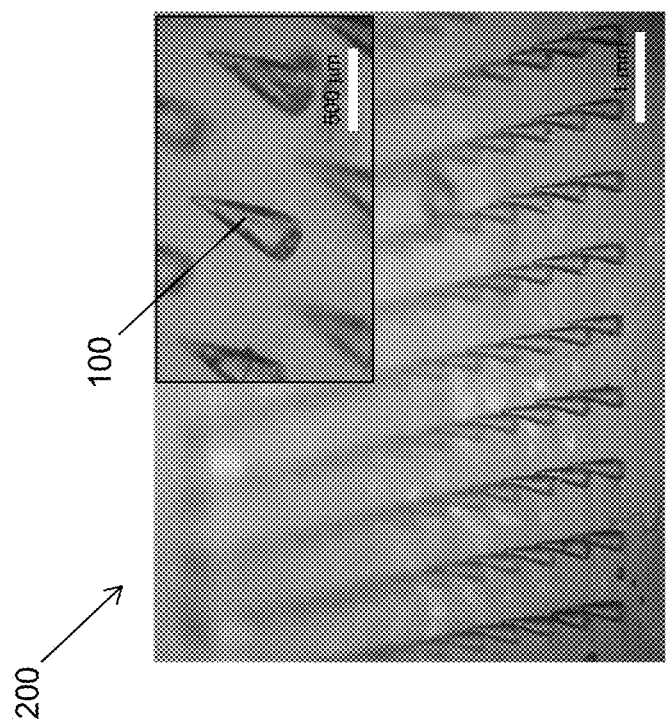
FIG. 2 is a photograph of a needle array.

Referring to FIG. 2, in some examples, an array 200 of double layer swellable needles 100 (referred to as a needle array) can be formed. Rigid needle arrays having stiff backings 103 (i.e., backings with a high modulus) can be formed. Flexible needle arrays having backings 103 with a low modulus can also be formed. The area density of swellable needles 100 in a needle array 200 can affect the level of adhesion of the needle array with tissue. In some examples, the density of swellable needles in the needle array can be 100 needles per cm$^2$ (e.g., a 10×10 array of needles per cm$^2$). Other needle densities are also possible.

In some examples, the backing 103 of a needle array can be formed of the same material as the outer layer 102, the core 104, or both. In some examples, the backing 103 of a needle array can be formed of a different material, e.g., to control the gas and liquid permeability of the backing 103 and/or to control the flexibility of the needle array. For instance, the backing 103 can be formed of a gas permeable and liquid impermeable material, such as Gore-Tex®, polydimethylsiloxane(PDMS), poly(ethylene terephthalate) (PET), and low-density polyethylene (LDPE). Such a backing can be useful to allow oxygen transfer through a needle array based adhesive bandage used on a skin wound. The backing 103 can also be formed of a gas impermeable and liquid impermeable material, such as crystalline polymer (e.g., high-density polyethylene (HDPE)) or a high molecular weight glass-like polymer (e.g., poly(methyl methacrylate) (PMMA)). In some examples, the backing 103 has one or more holes therein, such as a hole (e.g., a 2 mm hole) in the center of the backing 103 or one or more holes distributed over the backing. Such a backing can be useful to allow fluids to escape from under a needle array based adhesive bandage used on a skin graft.

In an alternative embodiment, double layer swellable needles can be designed such that delamination occurs at the interface between the core and the outer layer when the double layer swellable needles are removed from the tissue. In this embodiment, the materials of the outer layer and core can have little or no adhesion with each other. For instance, such double layer swellable needles can be formed of, e.g., a PS-b-PAA outer layer and a polylactic acid core. Such embodiments can be useful, e.g., for drug delivery, if the other coating contains the drug.

Figure 3B:
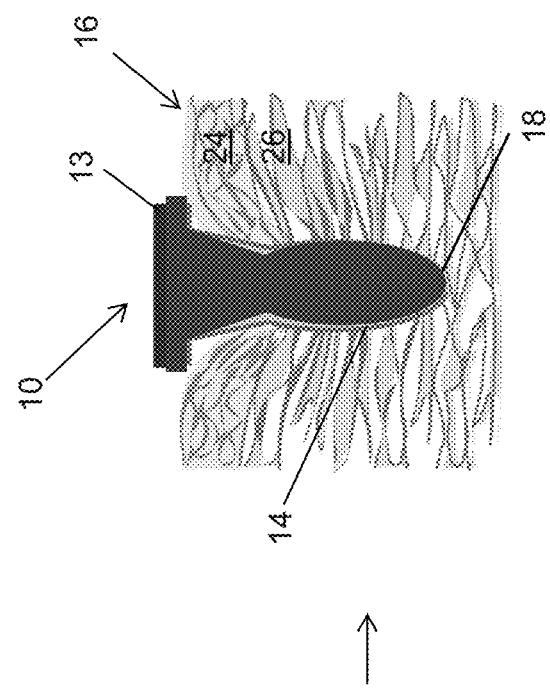
FIGS. 3A and 3B are diagrams of a single material swellable needle prior to and after penetration into skin, respectively.
Figure 3A:
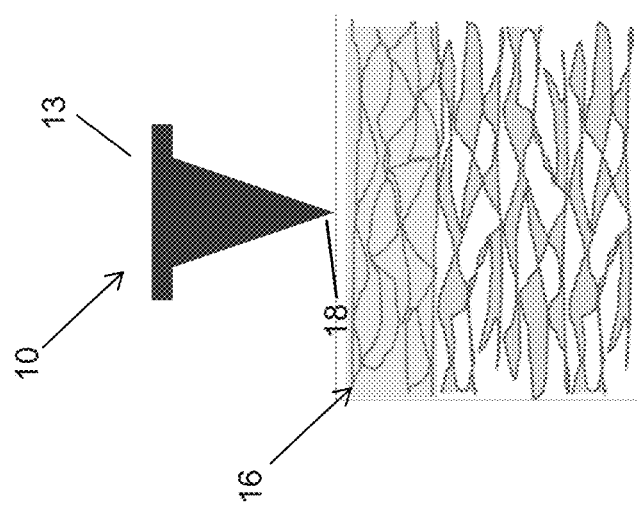

Referring to FIGS. 3A and 3B, in another alternative embodiment, a single material swellable needle 10 is a conical shaped needle formed of a single material and attached to a backing 13. In a dry (i.e., non-swollen) state (FIG. 3A), the single material swellable needle 10 is tapered to a point at a distal tip 18, enabling the single material swellable needle 10 to easily penetrate tissue 16. Upon insertion into the tissue 16 (FIG. 3B), the single material swellable needle 10 comes into contact with liquid in the tissue, the tissue 16 applies a compressive force to the single material swellable needle 10 and causing the single material swellable needle 10 to swell by absorbing liquid (e.g., water) from the tissue. The swelling of the single material swellable needle 10 causes a mechanical interlocking between the tissue and the swollen needle 10.

When the tissue 16 into which the single material swellable needle 10 is inserted has a stiff, compact outer layer 24 and an inner layer 26 that is less dense, the difference in stiffness between the outer layer 24 and the inner layer 26 of the tissue can allow more swelling at the distal tip 108 of the single material swellable needle 10 than along the length of the needle 10. This asymmetrical swelling results in the formation of a bulb 14. The bulb 14 locally deforms the tissue 16, mechanically interlocking with the tissue and anchoring the single material swellable needle 10 in place. In this swollen state, the single material swellable needle 10 can exhibit high levels of adhesion with the tissue 106 due to the ability of the swelling needle to asymmetrically push and deform the tissue.

In some implementations, the single material swellable needle 10 can be formed of a material that can swell in response to absorbing liquid from tissue, such as polymers. For instance, the single material swellable needle 10 can be formed of a water soluble polymer with a sol-gel transition temperature. In general, the single material swellable needle 10 can be formed of any of the materials described above for the outer layer 102 of the double layer needle 100 described above. In one example, the single material swellable needle 10 can be formed of a polymer, such as gelatin with a genipin cross-linker.

In some examples, an array 20 of single material swellable needles 10 (referred to as a single material needle array) can be formed. The backing 13 of the single material needle array 20 can be formed of the same material as the single material needles 10 or can be formed of a different material. In general, the backing 13 of the single material needle array 20 can have similar characteristics to the backing 103 of the needle array 200 described above and can be formed of any of the materials described above for the backing 103. For instance, in one example, the backing 13 can be formed of poly(lactic-co-glycolic) acid (PLGA).

In another alternative embodiment, the swellable needles are degradable in tissue. Degradable needles can find applications, e.g., for use in closing internal wounds; the swellable needles will degrade without the need for a follow-up surgery to remove the needles. Degradable needles can be formed of a degradable, non-swellable core and a degradable, swellable outer layer. Degradable needles can also be formed of a single material. Some examples of materials for use in degradable needles can include, e.g., polylactic acid and polycaprolactone.

Adhesion of Needle Arrays

Referring again to FIGS. 1A-1C, in the dry, non-swollen state, a swellable needle 100 is rigid (e.g., with a high modulus) and conically shaped, and thus able to penetrate tissue with a low insertion force. In its swollen state, the bulb 114 at the distal end of the swellable needle 100 causes local deformation of the surrounding tissue. This deformation allows the swellable needle to mechanically interlock with the tissue, enabling the swellable needle 100 to achieve a high level of adhesion with the tissue. The swollen outer layer is soft (e.g., with a lower modulus) and thus the swollen needles can be removed with sufficient pull-out force without significantly damaging the tissue.

Swelling of the outer layer 102 can occur quickly. For instance, in some examples the outer layer rapidly expands upon insertion into tissue, e.g., within the first one to three minutes after insertion. An equilibrium swollen state is reached slightly later, e.g., within about ten minutes after insertion, depending on the materials. The kinetics of water absorption by the outer layer of a double layer swellable needle can be significantly faster than the kinetics of water absorption of a bulk sample of the material of the outer layer. This difference may be due to the high surface area-to-volume ratio of the needle tips and the short diffusion length through the thickness of the outer layer, both of which enable water to penetrate quickly through the entire volume of the outer layer. The volume change upon swelling can be significant, e.g., about two to nine times (e.g., about three to four times), or more, of the original volume of the outer layer. In general, to achieve a high level of adhesion, the volume expansion of the outer layer can be maximized.

The level of adhesion of a needle array with tissue increases upon insertion of the needle array; the rate of increase of the level of adhesion is consistent with the swelling kinetics of the outer layer. At its equilibrium swollen state, a needle array can achieve a high level of adhesion with tissue. For instance, in one implementation, a 10×10 needle array over 1 cm$^2$ can achieve an adhesion strength to skin of at least about 0.6 N/cm$^2$, at least about 1.0 N/cm$^2$, or at least about 1.4 N/cm$^2$. Significant adhesion strength can be maintained even at high levels of strain between a needle array and tissue (e.g., during removal of the needle array) until the needle array is fully removed from the skin, indicating that needle arrays exhibit high adhesion energy. For instance, in certain embodiments, a 10×10 needle array over 1 cm$^2$ can achieve an adhesion energy to skin of at least about 0.5 J/cm$^2$, or at least about 1.0 J/cm$^2$.

The shape of the bulb 114 can also affect the level of adhesion of a swellable needle to tissue. For instance, referring again to FIGS. 1A-1C, the tip thickness t represents the thickness of the outer layer 102 at the distal tip 108 of the swellable needle 100. The tip thickness t affects the geometry of the swollen needle, which in turn affects the level of adhesion of the swellable needle to tissue. For instance, as the tip thickness t increases, the size of the swollen bulb 114 increases, which can cause the level of adhesion to increase. In some cases, beyond a threshold tip thickness (e.g., for a tip thickness t greater than about 70% of the overall length L of the swellable needle (i.e., t/L=70%)), the level of adhesion can begin to decrease and the likelihood of delamination between the outer layer 102 and the core 104 can increase. In some examples, swellable needles can be formed with dimensions t/L of between 20% and 70%, or about 40%.

The shape of the bulb 114 can also be affected by interfacial interactions between the material of the outer layer and the tissue. For instance, a bulb 114 with a larger surface area may form for a materials system in which the outer layer and the tissue have a low interfacial energy than for a materials system in which the outer layer and the tissue have a high interfacial energy. The size of the bulb can affect the adhesion of the swellable needle to tissue. For instance, a swellable needle with a smaller bulb 114 can exhibit a lower level of adhesion to tissue than a swellable needle with a larger bulb 114. The shape of the bulb can also affect the adhesion of the swellable needle to tissue. For instance, a swellable needle with a bulb 114 for which the swelling occurs primarily down (i.e., along the axis of the swellable needle) can exhibit a lower level of adhesion to tissue than a swellable needle with a bulb 114 for which the swelling includes an outward component.

Needle arrays exhibit high levels of adhesion with various types of tissue, including wet tissues such as skin and intestine tissue, and including tissues with various surface textures. Additionally, strong adhesion can be achieved to dynamic tissues (i.e., tissue that undergoes movement) during multiple cycles of movement.

Upon removal of a needle array from tissue, the outer layer of the double layer swellable needles begins to de-swell and returns to its original, stiff state. The kinetics of de-swelling can be comparable to the kinetics of swelling. For instance, the outer layer can return to its original state within about 15 minutes after removal from tissue. Needle arrays are robust to multiple cycles of swelling and de-swelling. Following recovery of shape and stiffness after removal from tissue, needle arrays can exhibit reversible adhesive properties during multiple swelling/de-swelling cycles. The needles can remain undamaged during these cycles and the level of adhesion between the needle array and the tissue can be consistent with each cycle.

Fabrication of Needle Arrays

Figure 4:
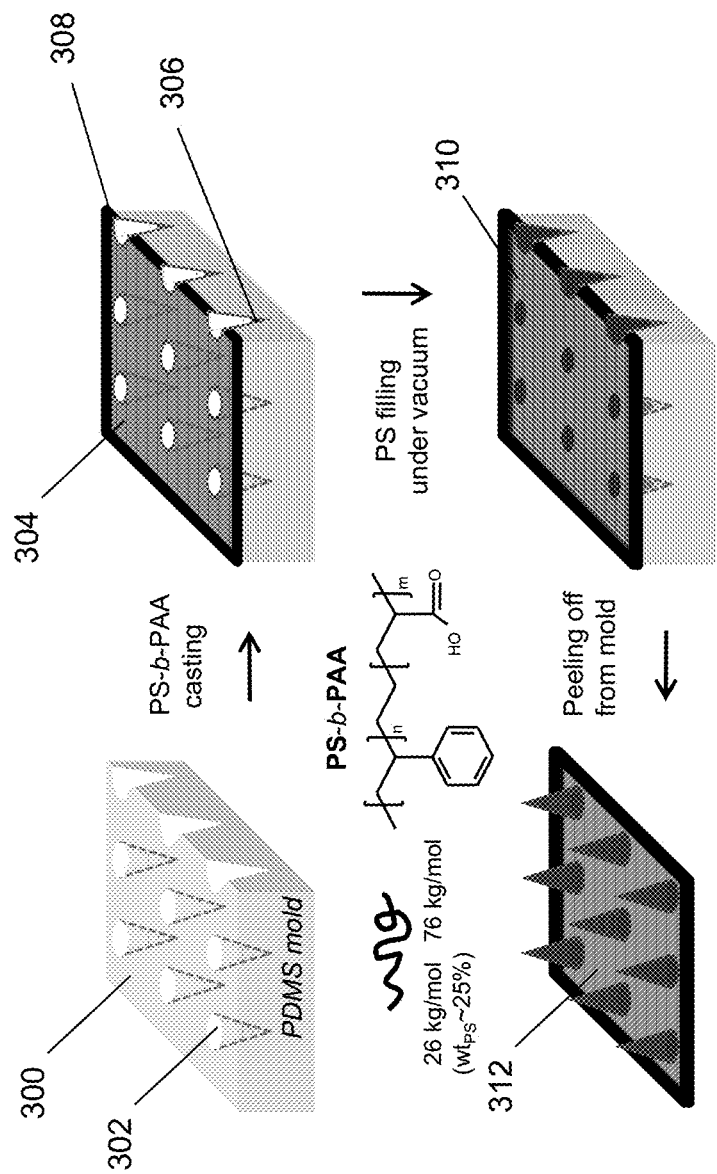
FIG. 4 is a flow diagram of a process for fabricating a double layer needle array.
Figure 5:
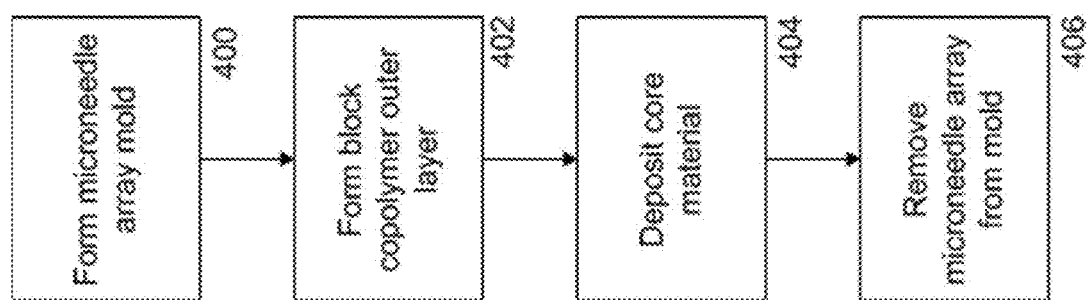
FIG. 5 is a flow chart of a process for fabricating a double layer needle array.

Referring to FIGS. 4 and 5, needle arrays can be fabricated using molding techniques. A needle array mold 300 can be formed (400) having conical holes 302 with positions and dimensions appropriate for the needle array that will be formed from the mold. The mold 300 can be formed of a material that is resistant to temperatures used in fabricating the needle array (e.g., a material heat resistant at least to 180° C.). For instance, the mold 300 can be formed of polydimethylsiloxane (PDMS) or elastic polymers.

In some examples, a female master mold is formed and a male mold is cast from the female master mold. Needle array molds 300 can be obtained by casting PDMS onto the male mold. For instance, a female master mold can be formed by depositing a resist layer onto a silicon wafer, e.g., by spin coating. The resist layer is exposed by ultraviolet (UV) light in the presence of a mask with a chrome dot pattern corresponding to the pattern of cavities to be formed in the female master mold. Following UV exposure, conically shaped areas of the resist that were blocked by the chrome dot pattern of the mask remain uncross-linked state. The resist is treated with an organic solvent (e.g., 1-Methoxy-2-propanol acetateacetone), to remove the uncross-linked areas, forming conical holes in the resist. The positions and dimensions of the conical holes 302 in the mold 300 can be easily controlled by fabrication parameters such as the UV exposure angle or the dimensions of the chrome dot pattern. In some examples, the female master mold can also be formed using standard photolithography, electron beam lithography, or other lithography techniques.

A male mold is formed by coating the master mold with the material of the male mold (e.g., PDMS), e.g., by replication with a curable prepolymer and cross-linker, spin coating, solvent casting, melt casting, or another deposition method, and allowing the material to dry. Needle array molds 300 can then be formed by depositing the material of the mold 300 (e.g., PDMS) onto the male mold, e.g., by replication with a curable prepolymer and cross-linker, spin coating, solvent casting, melt casting, or another deposition method, and allowing the material to dry.

In some examples, molds can be formed using additive processes such as three-dimensional printing, two-photon lithography, or another additive process. In some examples, molds can be formed using subtractive processes, such as etching by laser ablation (e.g., for molds formed of elastic polymers) or micromachining.

To form the outer layer of the double layer swellable needles, a layer 304 of a block copolymer material (e.g., PS-b-PAA) is coated onto the mold 300 (402). For instance, the layer 304 can be coated onto the mold by spin coating, solvent casting, melt casting, or another deposition method, followed by drying. Capillary forces during drying result in the formation of a thick film of material at the tip region 306 of each conical cavity 302. A thin film of material coats the walls of each conical cavity and forms a backing layer 308. The thickness of the film at the tip region 306 can be controlled by varying the concentration of block copolymer in the casting solution. For instance, solutions of 10 weight (wt) %, 18 wt %, and 25 wt % PS-b-PAA in dimethylformamide (DMF) can be solvent cast onto a mold 300 to fabricate double layer swellable needles with PS-b-PAA tip 306 thicknesses of 20%, 40% and 70%, respectively of the overall length of the conical cavities 302.

During casting and drying of the layer 304, the block copolymer self-assembles into multiple phases based on the interaction of the block copolymer with the mold. For instance, in a PS-b-PAA outer layer formed in a PDMS mold, PS migrates to the interface between the mold and the outer layer, forming a thin layer of PS at what will be the external surface of the needle array. This thin PS layer is believed to modulate the diffusion rate of water into the PS-b-PAA outer layer, thus preventing a rapid modulus drop caused by immediate water absorption by the PS-b-PAA outer layer upon insertion into tissue, which could result in insertion failure of the needle array.

To form the cores of the double layer swellable needles, a core material 310 (e.g., PS) is deposited onto the outer layer 304 (404), filling the conical cavities 302 and forming a second layer on the backing 308. For instance, the core material 310 can be coated onto the outer layer 304 by spin coating, solvent casting, melt casting, chemical vapor deposition, sputtering or evaporation of metals, or another deposition method, followed by drying. For example, to fabricate a rigid needle array, PS can be melted and casted at elevated temperature onto the PS-b-PAA outer layer under vacuum and then allowed to solidify at room temperature to form the PS core. During filling of the conical cavities 302 with melted PS, the PS block in the PS-b-PAA outer layer can entangle with the PS homopolymer core, causing interlocking between the core and the outer layer that can help prevent later delamination during removal of the double layer swellable needles from tissue. In addition, the carboxylic acid groups in the PAA chains can thermally cross-link via intermolecular anhydride formation during the high temperature casting of PS. To fabricate a flexible needle array, a flexible thermoplastic elastomer, such as styrene-isoprene-styrene, can be melt casted onto the PS-b-PAA outer layer. The needle array 312 can then be peeled off of the mold (406).

In some examples, a double sided needle array having an array of swellable needles on each side of the backing can be fabricated using two molds pressed together with the backing layer disposed between the two molds. In some examples, a double sided needle array can be fabricated by injection molding into a double sided mold.

Figure 6:
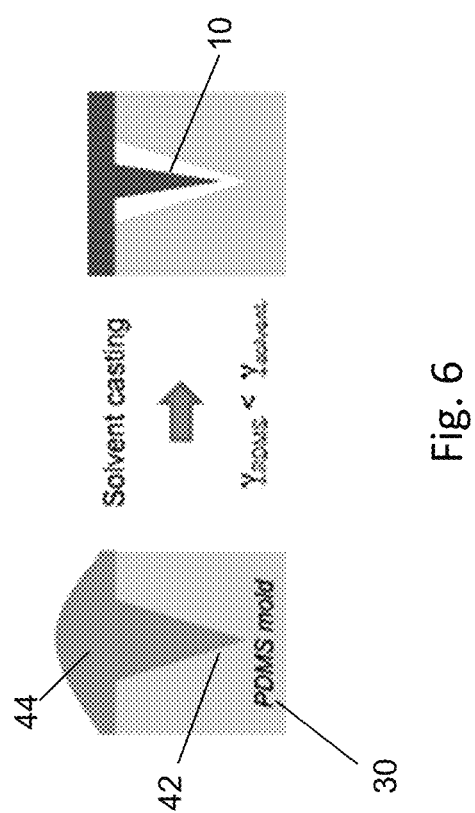
FIG. 6 is a flow diagram of a process for fabricating a single material needle array.

Referring to FIG. 6, single material needle arrays can also be fabricated using molding techniques. A mold 30 can be formed having conical holes 42 with positions and dimensions appropriate for the single material needle array that will be formed from the mold. The mold 30 can be formed of a material that is resistant to temperatures used in fabricating the single material needle array (e.g., a material heat resistant at least to 180° C.). For instance, the mold 30 can be formed of PDMS or elastic polymers. The mold 30 can be formed, e.g., as described above for the mold 300.

Applications and Uses of Needle Arrays

Swellable needles and needle arrays can be used for a wide range of applications. For instance, individual swellable needles and/or needle arrays can be used for drug delivery, cosmetics, blood and fluid sampling, and other applications. Needle arrays can be used as needle adhesives, e.g., as medical adhesives.

In some examples, needle arrays can be provided as reusable medical devices following medical applications can be reused following sterilization by ethanol or autoclave treatment. The robustness of needle arrays to multiple cycles of swelling and de-swelling can ensure that the performance of the needle arrays does not degrade during use.

In some examples, needle adhesives can be used as adhesive tapes or bandages, e.g., for external wounds such as cuts or surgical incisions or for internal wounds such as internal surgical incisions. For instance, needle adhesives can be used to replace and/or augment surgical sutures or surgical staples. In some examples, needle adhesives can have a backing that is gas permeable and liquid impermeable. Such a backing allows oxygen transfer while retaining moisture at the wound site, thus promoting healing. Needle adhesives have a high level of adhesion with both wet and dry tissue and thus are suitable for use at many sites, including skin and internal organ tissue. Needle adhesives also have a high level of adhesion with dynamic tissue (e.g., tissue at a joint that undergoes frequent movement).

In some examples, needle adhesives can be used as adhesives to affix adjacent tissues. Single-sided needle adhesives can be positioned across an interface between two adjacent tissues to hold the tissues together. Double-sided needle adhesives can be positioned between two adjacent tissues (i.e., within the interface between the tissues) to hold the tissues together. For instance, needle adhesives can be used to affix connective tissues including tendons and ligaments, e.g., to improve contact between tissues, or to seal tissues for the prevention of fluid leaks (e.g., in the intestine) or air leaks (e.g., in the lungs). Needle adhesives can also be used to prevent the formation of seromas following surgical operations that create dead space between layers of tissue (e.g., abdominoplasty), thus avoiding the use of drains that can increase the risk of infection and the likelihood of further surgery.

In some examples, needle adhesives can be used as adhesives to fix natural and synthetic skin grafts. Skin grafts are often employed for closure of open wounds resulting from burns, trauma, or surgical resections. For successful engraftment, continuous contact between the skin graft and the underlying tissue is important to assure graft survival. For instance, such contact provides for directed diffusion of wound bed nutrients and prevents the formation of hematomas or seromas.

Figure 7B:
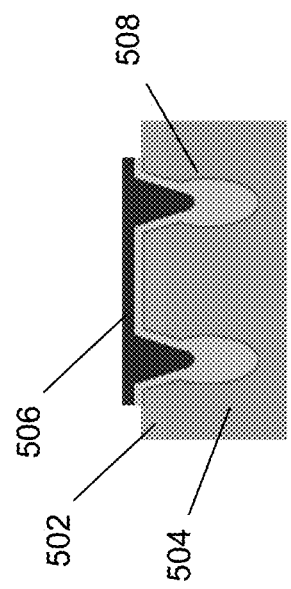
FIGS. 7A and 7B are diagrams of a skin graft closed with staples.
Figure 7D:
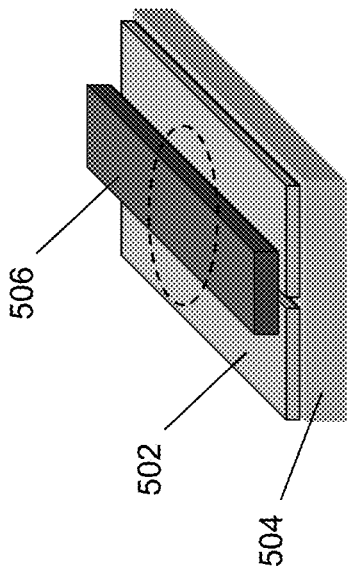
FIGS. 7C and 7D are diagrams of a skin graft closed with a needle adhesive.
Figure 7A:
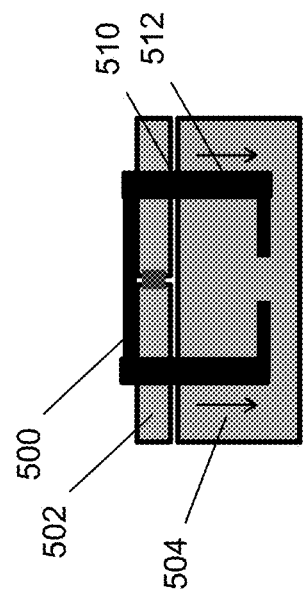
Figure 7C:
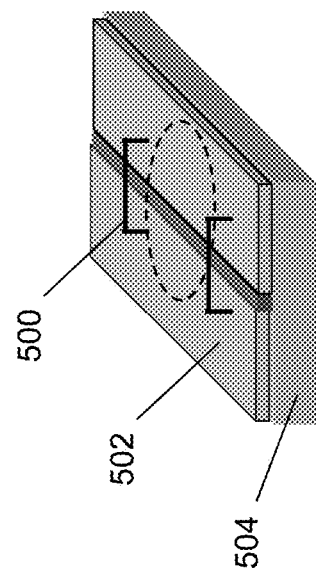

Referring to FIG. 7A, surgical sutures or staples 500 applied to the perimeter of a skin graft 502 on an underlying wound bed 504 represent the current standard of care in affixing skin grafts. Referring to FIG. 7C, a needle adhesive 506 applied to the skin graft provides intimate contact between the skin graft 502 and the wound bed 504 over the entire surface area of the wound. The needle adhesive 506 can maintain contact between the skin graft 502 and the wound bed 504 even during movement of the wounded patient and thus can help preserve the graft with reduced use of secondary dressings or grafted body part immobilization. One or more drainage holes in the backing of the needle adhesive 506 can prevent accumulation of fluid at the interface between the needle adhesive 506 and the skin graft 502.

In some examples, needle adhesives can provide a biological barrier against bacterial infiltration, thus reducing the risk of infection at a skin graft, surgical site, or other wound site. Referring to FIG. 7D, in the example of a skin graft, the interlocked and swollen needles 100 of the needle adhesive 506 tightly seal holes 508 punctured in the skin graft 502 by the needles themselves. This tight fit of each swellable needle 100 in its own hole 508 prevents bacterial infiltration into the graft site. As a result, the risk of infection to the burn tissue can be reduced. Referring to FIG. 7B, in the case of staple or suture fixation, stress concentrations localized around the legs 510 of the staples 500 can cause tearing of the skin graft 502, producing a hole 512 larger than the diameter of the corresponding leg 510 that can serve as a pathway for bacterial infiltration.

In some examples, needle adhesives can also be used for other medical adhesive applications, e.g., to provide adhesion during minimally invasive procedures, ophthalmologic procedures, or cardiac procedures. Needle adhesives can be used to affix medical devices, e.g., to temporarily anchor medical devices, such as catheters, in place. Needle adhesives can be used to affix bandages, gauze, medical tapes, temporary tattoos, stents, meshes (e.g., biodegradable meshes or nonbiodegradable meshes) or other materials to a patient. Needle adhesives can be used to secure needles (e.g., dialysis needles) or trocars in place such that tissue damage during penetration and removal can be reduced. Needle adhesives can also be used for orthopedic applications such as the attachment of tendons or ligaments to bone, the attachment of cartilage, or the fixation of devices or constructs to cartilage, liver, lung, pancreas, or other tissue or sites. Needle adhesives can also be used in conjunction with staples to enhance adhesion. For instance, the ends of the staples can be formed in the shape of a single material swellable needle or a double layer swellable needle in order to promote adhesion, deliver drugs to the staple site, or both. In some cases, using staples with swellable needle-like ends can reduce or eliminate the need to bend staples to secure the staples in place. Needle adhesives can also be used in dental applications, e.g., for guided bone regeneration. Other medical applications are also possible.

In some examples, one or more swellable needles can be used for delivery of substances. For instance, an individual swellable needle or a needle array can be loaded with one or more substances for delivery directly into the tissue in a minimally invasive manner. Swellable needles can be used to deliver drugs, small molecules, nanoparticles, microparticles, biomolecules, and other substances. "Biomolecules," as used herein, refers to molecules (e.g., proteins, amino acids, peptides, polynucleotides, nucleotides, carbohydrates, sugars, lipids, nucleoproteins, glycoproteins, lipoproteins, steroids, or other molecules), either naturally-occurring or artificially created (e.g., by synthetic or recombinant methods), that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, siRNA, aptamers, DNA, RNA, proteins, peptides, polysaccharides and any combinations of these components. In addition, a wide variety of drugs can be loaded into the swellable needles, including, e.g., therapeutic agents, such as antibacterial agents, pro-regenerative agents, anti-inflammatory agents, or other therapeutic agents; analgesic agents; vaccines; or other drugs.

In some examples, one or more swellable needles (e.g., an individual swellable needle or a needle array) can be used to deliver one or more drugs directly into a wound environment, e.g., to deliver an antibiotic to a skin graft. In some examples, a transdermal skin patch can be formed of a needle adhesive and used to deliver a systemic dose of a drug, such as an anti-nausea agent. In some examples, one or more swellable needles can be used for cell delivery. For instance, lyophilized cells can be provided to tissue via a needle array for in situ thawing. In some examples, one or more swellable needles can be used to deliver a vaccine; for instance, large swellable needles loaded with a vaccine can be used to vaccinate herds of cattle. In some examples, one or more swellable needles can be used to deliver an agent, such as a flavor agent, to a fruit or vegetable, such as a tomato.

Drugs can be loaded into an individual swellable needle or a needle array in a variety of ways. In some examples, dry swellable needles can be soaked in a solution containing the drug to dope the swellable outer layer. The doped swellable needles can then be dried and returned to their stiff, unswollen state. Upon insertion into tissue, the outer layer swells, releasing the drug into the tissue. The drug release can be gradual, e.g., over a period of hours or days (e.g., over a period of about six days). In some examples, a swellable needle can have a hollow lumen through the center of the core. The hollow lumen can be connected to a drug reservoir, e.g., in the backing of the needle array or in a separate reservoir connected to the hollow lumen via a microfluidic flow channel. The hollow lumen can be connected to a hole in the distal tip of the swellable needle such that the drug is dispensed through the hole. The hollow lumen can also be used to provide a continuous feed of drug to the swellable outer layer, allowing for long term controlled release of the drug into the tissue. Other approaches to swellable needle drug delivery are also possible.

In some examples, individual swellable needles or needle arrays can be used to prepare sites for drug delivery. For instance, one or more needles can be used to puncture skin, cartilage, muscle, or other tissues, to create one or more holes. When the needles are removed, a hole is present into which drugs or other substances can be deposited.

In some examples, individual swellable needles or needle arrays can be used for cosmetic applications, for instance, to deliver cosmetic substances (e.g., Botox®), UV blocking substances (e.g., $TiO_2$ or ZnO nanoparticles), or anti-scar agents to the skin. Using a needle array to deliver cosmetic substances enables the substance to be uniformly distributed across the skin. In addition, the small holes in the skin that are created by swellable needles can make the delivery of the cosmetic substances less painful. In some examples, individual swellable needles or needle arrays can be used for the therapeutic removal or damage of epidermal tissue, also known as dermabrasion, which can help promote wound healing, tissue response, or tissue regeneration.

In some examples, individual swellable needles or needle arrays can be used for local sampling of blood or other biological fluids. When a swellable needle is inserted into tissue, the outer layer of the needle swells, absorbing fluid from the surrounding tissue. Swollen needles can be removed from the skin and the absorbed fluid can be collected (e.g., by drying and de-swelling the needles or by simply squeezing the bulb of the needle) and analyzed.

In some examples, needle adhesives can be used in underwater applications, e.g., for underwater medical treatments, due to their high level of adhesion in wet environments.

In some examples, needles can be adapted to millimeter scale applications, e.g., for the anchorage of drainage and infusion catheters and needles. For instance, needles and catheters typically used to access a site within the body for long term infusion or drainage may benefit from improved anchorage by positioning with a needle adhesive. One or more swellable needles can be used as hernia tacks.

In some examples, needle adhesives can be used to join dead animal tissues, for instance, for experimental purposes, cooking, taxidermy, or other applications.

In some examples, swellable needles can be adapted to larger scale applications, such as centimeter or meter scale applications, e.g., for anchoring materials together in a construction application.

EXAMPLES

The invention is further described in the following examples, which do not limit the scope of the invention described in the claims.

The following examples generally show the fabrication and morphology of swellable needles and needle arrays, demonstrating the shape change that occurs upon insertion of a swellable needle into a liquid-containing substrate. The examples further demonstrate the adhesion properties of needle arrays. In addition, example applications of needle arrays are demonstrated, including the use of needle arrays as adhesives to affix skin grafts, the ability of needle arrays to act as bacterial barriers, the ability of needle arrays to adhere to intestine tissue, and the use of swellable needles for drug delivery.

Example 1—Fabrication of a Needle Array

Needles arrays with a polystyrene-block-poly(acrylic acid) PS-b-PAA outer layer and a polystyrene (PS) core were fabricated by molding techniques.

PS-b-PAA was prepared by hydrolysis of polystyrene-block-poly(tert-butyl acrylate) (PS-b-PtBA) (0.5 g, $M_n$: 26 k for PS, $M_n$: 128 k for PtBA, polydispersity index (PDI): 1.25, Polymer Source, Inc., Montreal, Quebec) in dry dichloromethane (20 mL) with trifluoroacetic acid (1.2 molar equivalent compared to tert-butyl ester groups) as a catalyst for 48 hours. PS-b-PAA was precipitated into hexane, filtered, and washed several times to remove any trace of the catalyst. Complete conversion of PtBA to PAA polymer was confirmed by $^1H$ nuclear magnetic resonance (NMR) (dimethylformamide (DMF)-d7). A peak at 1.45 ppm corresponding to methyl ester protons of tert-butyl acrylate (tBA) was observed prior to hydrolysis and disappeared after hydrolysis. A hydroxyl peak at 12.6 ppm corresponding to a carboxylic acid group appeared after hydrolysis. These NMR results indicate that tBA was fully converted to acrylic acid during hydrolysis.

The number average molecular weight ($M_n$) of PS-b-PAA used for the outer layer of the swellable needles was 26 kg $mol^{-1}$ for PS and 76 kg $mol^{-1}$ for PAA, with a PS weight fraction of about 25%. The stiffness of PS-b-PAA with 25% weight fraction PS in its swollen state approximates the stiffness of skin or intestine tissue. Other compositions of PS-b-PAA were also prepared by hydrolysis of PS-b-PtBA ($M_n$: 19 k for PS, $M_n$: 729 k for PtBA, PDI: 1.23; and $M_n$: 24 k for PS, $M_n$: 36 k for PtBA, PDI:1.09, Polymer Source, Inc.) as described above.

A 1 $cm^2$ female polydimethylsiloxane (PDMS) mold with a 10×10 array of conical cavities were prepared using inclined ultraviolet (UV) photolithography and molding techniques. To fabricate a female master mold, a 1 mm thick film of SU-8 photoresist (MicroChem corp., Newton, Mass.) was spin-coated onto a silicon wafer and exposed to UV light (365 nm, 10 $W/cm^2$) through a chrome mask patterned with 300 µm diameter dots. The UV exposure was performed at an angle of 20° on a rotating stage at 10 rpm for 450 seconds. The unexposed region in the photoresist film (i.e., the region blocked by the chrome mask) was developed by treatment with 1-Methoxy-2-propanol acetateacetone. The resulting conical cavities in the female master mold were 700 µm deep with a base diameter of 280 µm and a tip radius of 10 µm. The tip-to-tip spacing between cavities was 950 µm. Individual PDMS (Sylgard 184, Dow Corning, Midland, Mich.) molds were obtained from male PDMS molds cast from the female master mold.

Negative conical needles in a PDMS mold were fabricated with a base diameter of 280 µm, a tip diameter of 10 µm, and a length of 700 µm. The outer layer of the swellable needles was prepared by solvent casting PS-b-PAA dissolved in DMF for 48 hours followed by degassing.

Figure 8A:
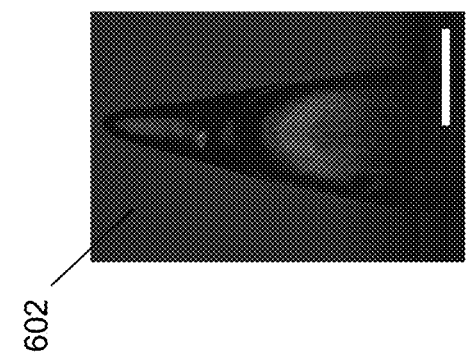
FIGS. 8A-8C are optical microscopy images of hollow double layer swellable needles with different PS-b-PAA fractions. The scale bar is 200 µm.
Figure 8B:
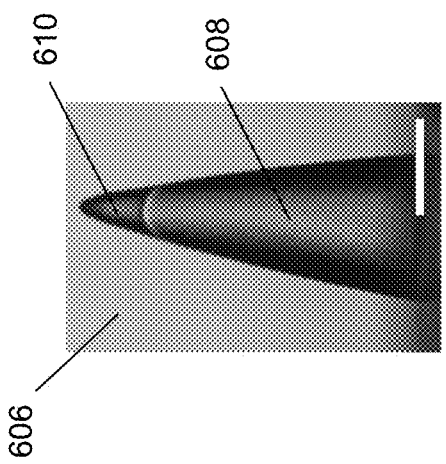
Figure 8C:
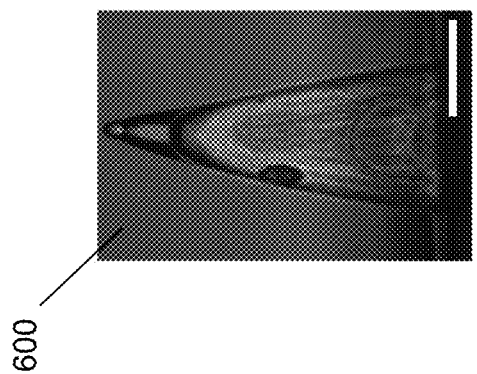

Solutions of 10 weight (wt) %, 18 wt %, and 25 wt % PS-b-PAA were used to fabricate needle arrays with PS-b-PAA tip thickness 20%, 40% and 70%, respectively. Cross-sectional optical images of these swellable needles 600, 602, 604 are shown in FIGS. 8A-8C, respectively.

Figure 8D:
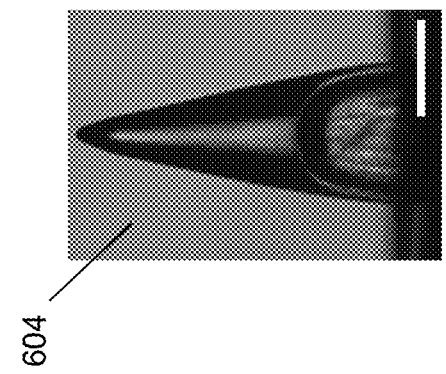
FIG. 8D is an optical microscopy image of a double layer swellable needle filled with a PS core. The scale bar is 200 µm.

Rigid needle arrays were fabricated by melting PS pellets (Mw: 100 k, PDI: 1.06, Polysciences, Inc., Warrington, Pa.) onto the solvent-casted PS-b-PAA outer layer at 180° C. under vacuum and then stored under vacuum for 4 hours to form the PS core. After cooling to room temperature, the needle arrays were gently peeled from the PDMS mold. A cross-sectional optical image of a PS-filled swellable needle 606 with a PS-b-PAA tip thickness of 20% (t/L) is shown in FIG. 8D. The PS core 608 completely fills the cavity in the outer layer 610 and makes good contact with the outer layer 610.

Flexible needle arrays were fabricated by melt casting styrene-isoprene-styrene copolymer (weight fraction of PS: 22%, Sigma-Aldrich, St. Louis, Mo.) onto the solvent-casted PS-b-PAA outer layer.

The composition of the PS-b-PAA outer layer at its interface with air and at its interface with the PS core was examined by performing X-ray photoelectron spectroscopy (XPS) on PS-b-PAA films casted onto PS and PDMS substrates. The theoretical C/O ratio for PAA is 1.5. XPS results indicated that the C/O ratio at the surface of the PS-b-PAA layer on PDMS was 14.9 and that the C/O ratio at the surface of the PS-b-PAA layer on PS was 22.3, suggesting that PS was the dominant interfacial block. These results suggest that a loosely-packed PS film with a thickness of about 10 nm forms at the surface of the PDMS (i.e., at the interface of PS-b-PAA with air following removal of a needle array from a mold). This thin PS layer is believed to modulate the diffusion rate into the PS-b-PAA outer layer, thus preventing a rapid modulus drop caused by immediate water absorption by the PS-b-PAA outer layer upon insertion into tissue, which could result in insertion failure of the needle array.

Single material needle arrays formed of gelatin with a genipin cross-linker were fabricated by molding techniques. A PDMS mold having conical cavities 42 was prepared as described above. Porcine skin gelatin powder (Sigma-Aldrich) was dissolved in water at 50° C. and a genipin was added (1 wt % on dry gelatin basis) to make a 16 wt % gelatin solution. This prepared casting solution was casted onto the PDMS mold at 50° C. for 12 hours to form the single material needle array. To form a PLGA backing on the single material needle array, a PLGA film was placed onto the single material needle array casted onto the PDMS mold and pressed with a hot pin stub to melt the PLGA, connecting the PLGA backing to the single material needle array.

Figure 9:
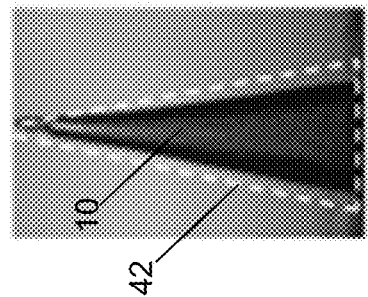
FIG. 9 is an optical microscopy image of a single material swellable needle.

When casting single material needles from an aqueous solution onto a hydrophobic mold, such as PDMS, the single material needles shrink as the solvent is evaporated because the solvent has a surface tension ($\gamma_{water}$=72.8 mN/m at 20° C.) greater than the surface tension of the mold ($\gamma_{PDMS}$=21.3 mN/m at 20° C.). Casting a water soluble polymer at a temperature higher than the sol-gel transition temperature of the polymer can help to mitigate the shrinkage of the needles. Referring to FIG. 9, solvent casting of gelatin-genipin single material needles 10 from a water solution produced resulted in a 20% shrinkage relative to the size of the mold cavities (indicated with a dashed line).

Example 2—Swellable Needle Insertion into Hydrogel

To observe the real-time swelling behavior of swellable needles upon insertion into a hydrogel substrate, one row of swellable needles was cut from a needle array and attached to a metal specimen with double-sided tape. The row of needles was inserted into a transparent 1.4 wt. % agarose hydrogel supported by a fixed metal plate and an overhanging plastic substrate. Swelling of the needles was recorded using an inverted microscope upon insertion of the swellable needles into the hydrogel and upon removal of the swellable needles from the hydrogel.

Figure 10A:
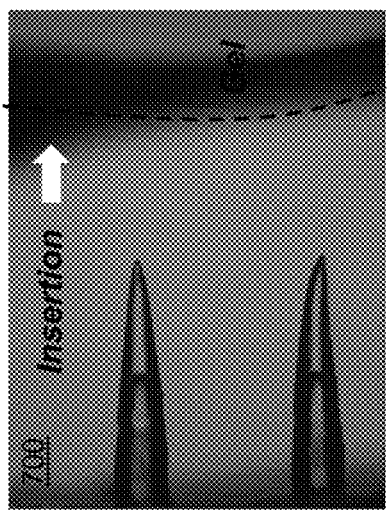
FIGS. 10A-10C are optical microscopy images of the insertion of double layer swellable needles into a hydrogel.
Figure 10B:
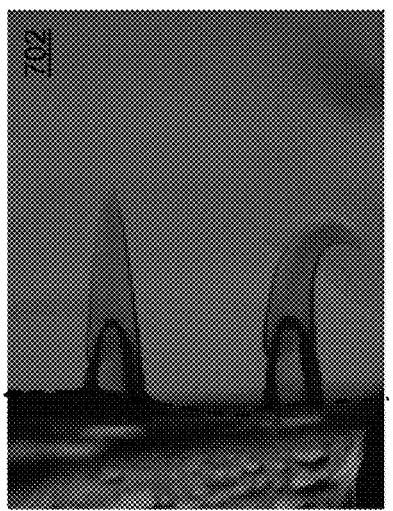
Figure 10C:
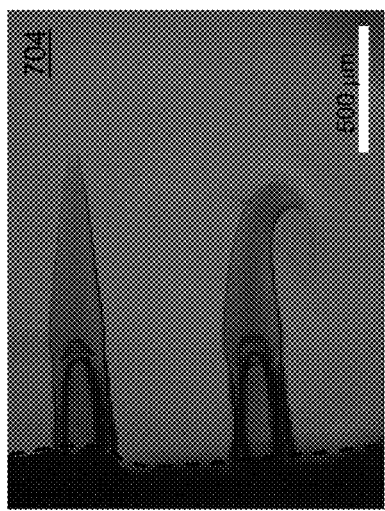

Referring to FIGS. 10A-10C, the swellable needles prior to insertion into the hydrogel (image 700) had a tip thickness of about 40% of the total needle length. Upon insertion into the hydrogel, the volume of the PS-b-PAA outer layer rapidly increased and reached 60% of the maximum swollen state within one minute (image 702). Tip swelling equilibrated within ten minutes (image 704). The volume expansion by swelling of the outer layer occurred predominantly axially in the tip region.

Figure 11:
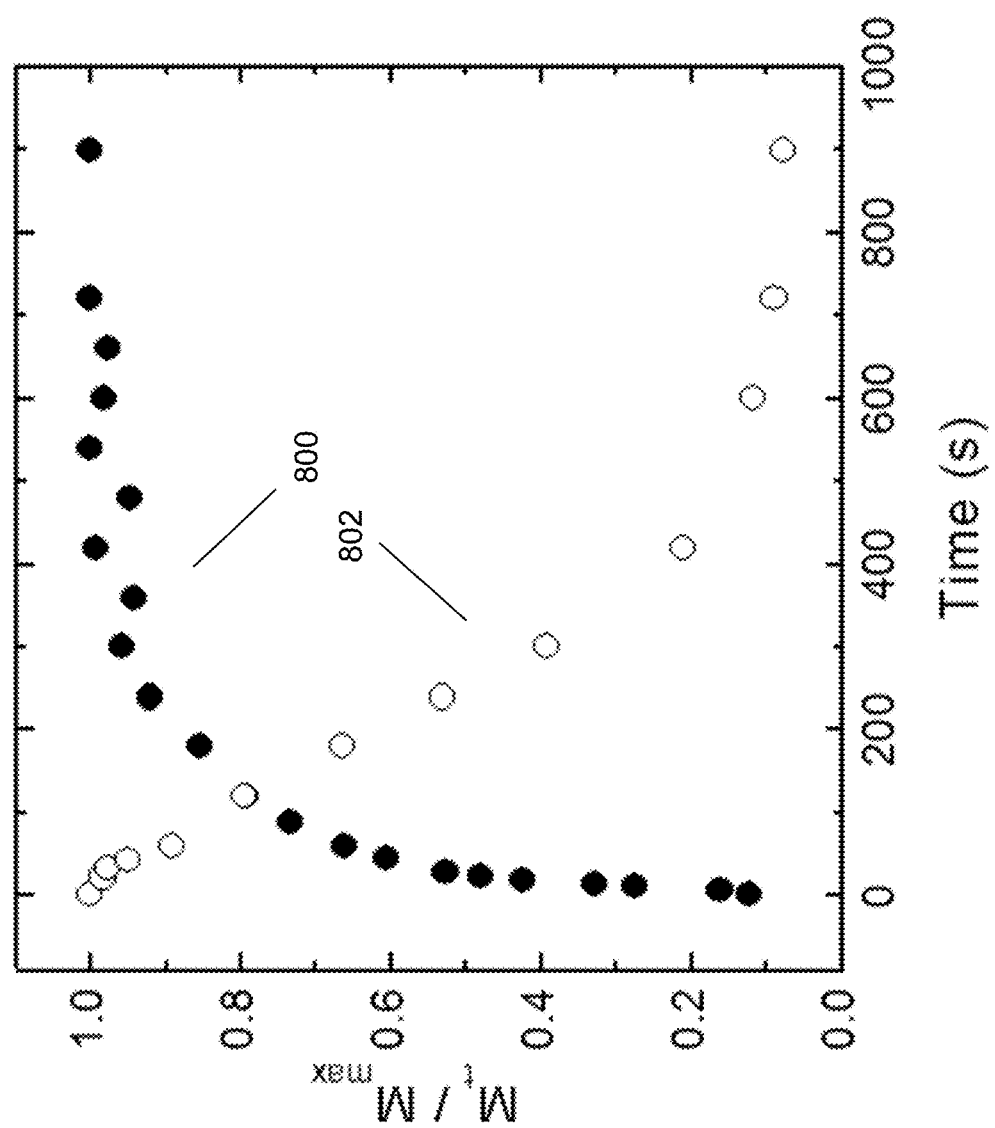
FIG. 11 is a plot of swelling and de-swelling kinetics for double layer swellable needles inserted into and removed from a hydrogel, respectively.
Figure 12A:
FIGS. 12A-12D are optical frequency domain images of double layer swellable needles inserted into muscle tissue.
Figure 12B:
Figure 12C:
Figure 12D:
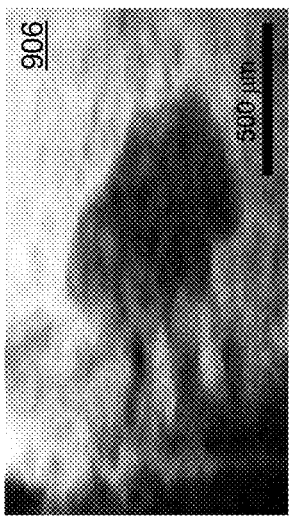

Referring to FIG. 11, the swelling kinetics (curve 800), measured by the change in volume of the outer layer, reflect the rapid increase in tip volume and the eventual equilibration of tip swelling. At equilibrium, the volume of the PS-b-PAA outer layer had expanded to about nine times its initial volume, where Mt is the absorbed amount of water at time t and $M_{max}$ is the absorbed amount of water in the maximum swollen state of the outer layer. The kinetics of water absorption by the PS-b-PAA outer layer are significantly faster than those of bulk PS-b-PAA with mm-scale thickness. This difference may be due to the high surface area-to-volume ratio of the swellable needle tips and the short water diffusion length.

The swollen needles interlocked with the hydrogel but could still be removed from the hydrogel without breakage or delamination. As shown in curve 802, the swollen tips immediately began to deswell following removal from the hydrogel and fully returned to their original conical shape within about 15 minutes.

Needles of other compositions were inserted into the agarose hydrogel as controls. Non-swellable needles formed only of PS (fabricated by melting PS pellets in molds at 180° C. under vacuum for 4 hours) were easily inserted into the hydrogel but did not interlock with the hydrogel and were freely removed without significant applied force. Needles with a flexible PAA outer layer and a PS core were unable to penetrate the hydrogel because of the low mechanical strength of PAA. Stiff needles formed only of PAA (fabricated by cross-linking following a harsh thermal treatment) can be inserted into the hydrogel but are prone to delamination from the backing during removal due to poor interfacial adhesion between PAA and the backing layer.

Example 3—Swellable Needle Insertion into Tissue

Optical Frequency Domain Imaging (OFDI), a second generation Optical Coherence Tomography (OCT) technology, was used to assess the shape change of swellable needles upon insertion into animal tissue.

OFDI is capable of providing non-invasive cross-sectional views of internal tissue structures to a depth of about 1-2 mm with high resolution. Light from a wavelength-swept laser source (1220-1360 nm) was split into reference and sample arms by means of a fiberized interferometer. The sample light was focused into a spot with a 30 μm waist radius and scanned over the tissue. The reflected light was recombined with the reference signal prior to detection, digitized, and reconstructed to yield a depth resolved scattering profile at each scanning position.

Swellable needles were inserted frontally into a cube of chicken muscle, close to the top tissue surface to enable imaging with OFDI. An area of 5×3 mm, including 1024× 512 depth profiles, was scanned at two minute intervals. The reconstructed cross-sectional images showed signal void regions in the area of the swellable needles and a high scattering signal from the surrounding tissue. Minimum intensity projections along the lateral direction of the swellable needles were taken after smoothing the tomograms to reduce speckle, providing a clear view of the shape profile of the swellable needles.

Referring to FIGS. 12A-12D, a conical swellable needle was inserted into muscle (image 900). While the swellable needle inserted into muscle tissue showed a lower initial volume expansion rate than the swellable needles inserted into the agarose hydrogel, the swellable needle in muscle tissue also reached its final swollen state within ten minutes. The insertion into muscle induced radial expansion of the swellable needle (images 902, 904, 906). The swollen needle formed a mushroom-shaped structure, the geometry of which is well-suited to support mechanical interlocking with tissue.

Example 4—Adhesion of Needle Adhesives

The adhesion properties of a needle adhesive were evaluated by testing the normal adhesion strength of a 1 cm$^2$ (10×10 swellable needles) needle array on fresh cadaveric porcine skin.

To prepare the porcine skin, full thickness porcine cadaver skin was stored frozen and cut into ~2 cm×2 cm patches followed by immersion in phosphate buffered saline (PBS) for 1 hour. For semi-dry adhesion tests, water was removed from the surface of porcine skin with blotting paper and the skin was dried on blotting paper for several minutes until about 10-20% of the absorbed water was removed. For wet adhesion testing, 200 µL of PBS buffer was spread across the surface of porcine skin before adhesion tests.

Normal adhesion tests for samples with an area of 1 cm$^2$ were performed using an eXpert 760 mechanical tester (ADMET, Inc., Norwood, Mass.) with custom-fabricated stainless steel tissue grips and a 50 N load cell. A flat section of skin tissue was affixed using cyanoacrylate glue to a test fixture (i.e., pin mount stub with diameter of 25.4 mm) and mounted within the lower grips at the base of the mechanical tester. The needle array (10×10 swellable needles in 1 cm$^2$) or flat control patch was glued onto the opposing test fixture and fixed between the upper grips of the mechanical tester. Test samples were applied to tissues with 10 N of preload at 100 mm/min and held in position for 2 minutes, 5 minutes, 10 minutes, 30 minutes, or 6 hours. Samples were displaced at a rate of 1 mm/min and the force was recorded.

Adhesion tests were conducted to investigate the time-dependent effect of swelling-induced swellable needle shape change on adhesion as compared to the adhesion of non-swellable PS needles. Needle arrays formed of swellable needles with a swellable tip thickness (t/L) of 20% (referred to as BCP (block copolymer) needles (20%)) and a swellable tip thickness of 40% (referred to as BCP needles (40%)) relative to the total length of the swellable needle were tested. Needle arrays of PS needles were also tested. Adhesion of flat PS-b-PAA (BCP) and PS films were measured as controls. The adhesion strength of each needle array or flat sample to porcine skin was measured two minutes and ten minutes after insertion into or contact with the skin.

To fabricate flat block copolymer (BCP) PS-b-PAA films as controls for adhesion testing, PS-b-PAA was solvent casted on PDMS flat substrates (1 cm×1 cm×0.5 cm square well) for 48 hrs and then PS was filled by melt casting at 180° C. for 4 hrs. Flat PS films were prepared by melt casting flat PDMS molds with PS.

Figure 13A:
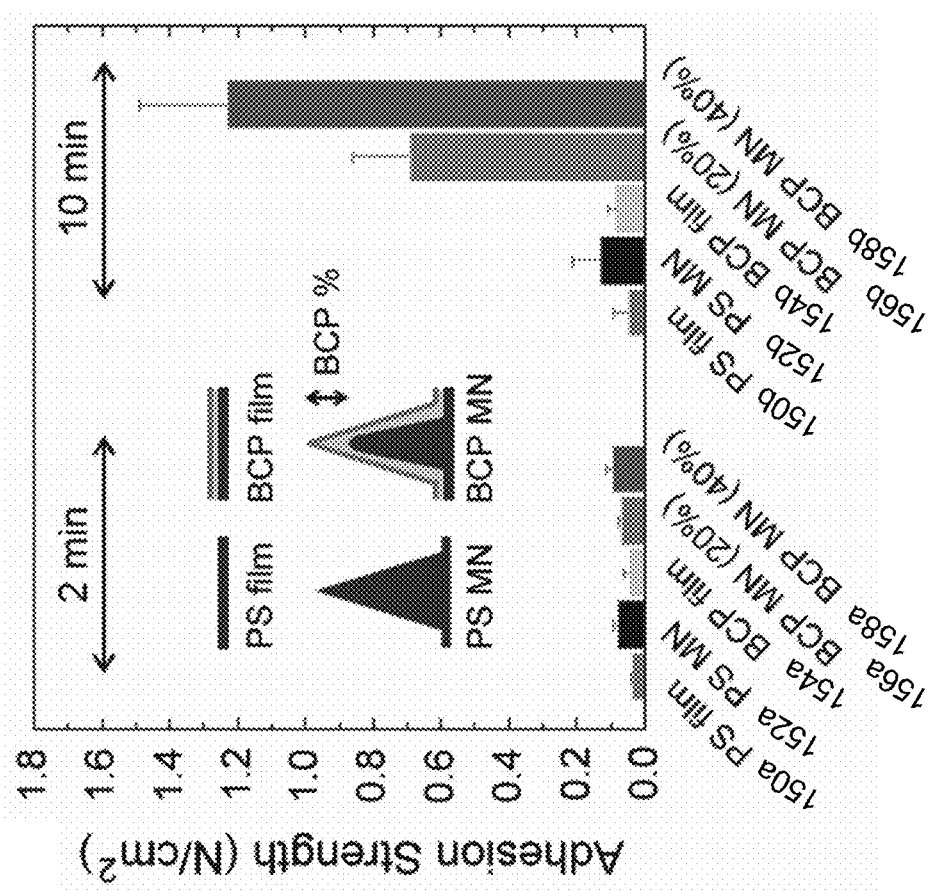
FIG. 13A is a plot of the adhesion strength of various materials to pig skin.

Referring to FIG. 13A, both flat PS films and flat BCP films showed low adhesion strength to skin (less than 0.1 N/cm$^2$) at both two minutes (bars 150a, 154a, respectively) and ten minutes (bars 105b, 154b, respectively) after contact with the skin.

Figure 14:
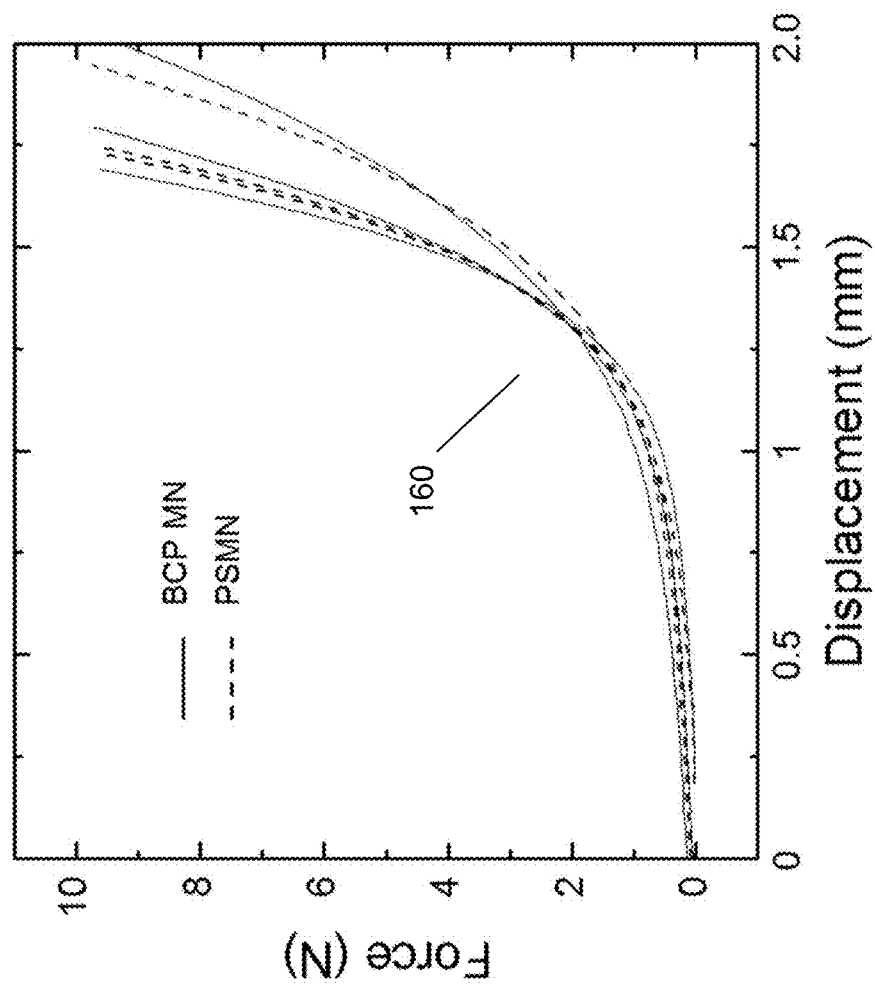
FIG. 14 is a plot of force versus displacement for the insertion of a double layer needle array into pig skin.

Two minutes after insertion, PS needle arrays (bar 152a), BCP needle (20%) arrays (bar 156a), and BCP needle (40%) arrays (bar 158a) all exhibit similar adhesion strengths. Referring also to FIG. 14, PS needle arrays and BCP needle (40%) arrays also showed similar force versus displacement profiles 160 during insertion (n=3).

Ten minutes after insertion, the maximum swollen state for the BCP swellable needles was achieved and the adhesion strength of the BCP needle array (bars 156b, 158b) dramatically increased. The adhesion strength of the PS needle array (bar 152b), which did not undergo a shape change, did not change from its value at two minutes. The BCP needle (20%) array showed an adhesion strength (0.69±0.17 N/cm$^2$) about seven times higher than that of PS needles (0.098±0.015 N/cm$^2$). Furthermore, the BCP needle (40%) array exhibited an approximately twelve-fold increase in adhesion strength over their initial adhesion strength.

Figure 13B:
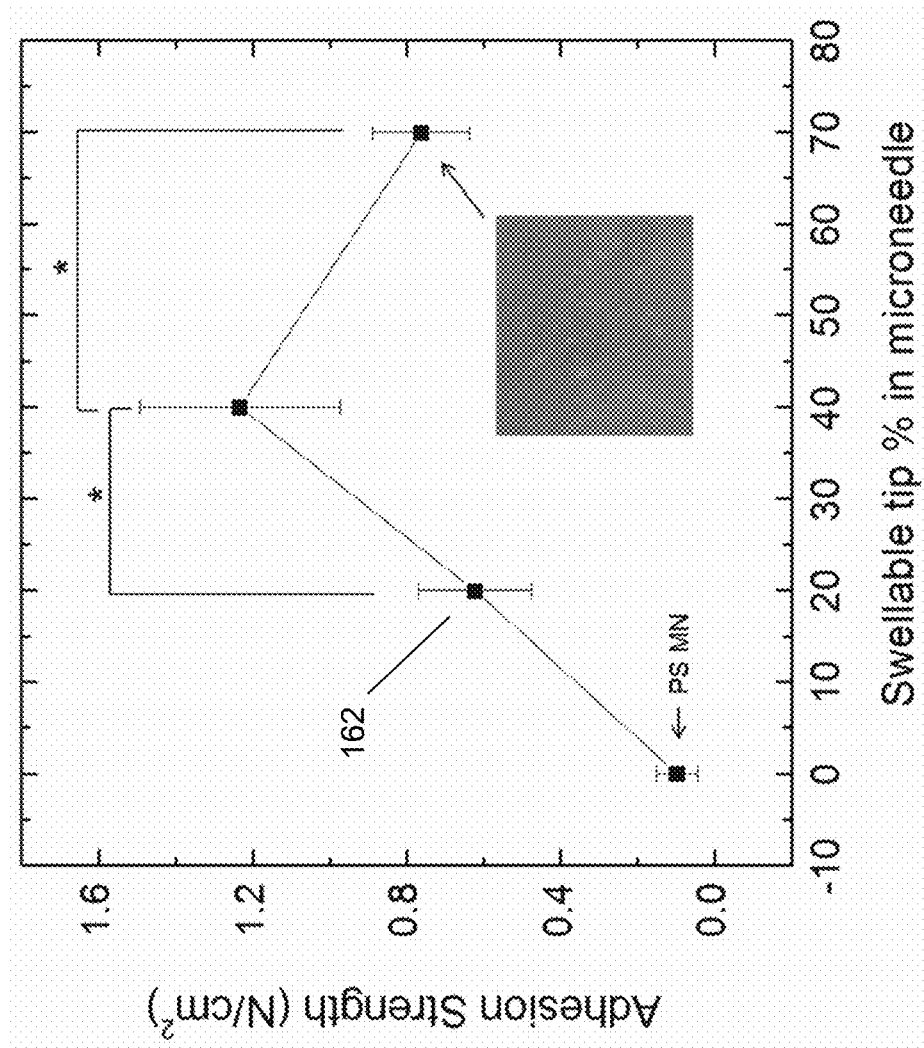
FIG. 13B is a plot of the adhesion strength of double layer swellable needles with various swellable tip thicknesses to pig skin.

Referring also to FIG. 13B, a BCP needle array formed of BCP swellable needles with a swellable tip thickness of 70% exhibited lower adhesion strength than the BCP needle (40%) array, as shown in curve 162. This decrease in adhesion may be due to a less favorable configuration for interlocking with tissue. In addition, the swollen tips of the BCP swellable needles (70%) delaminated during pull-out from the skin.

Figure 15:
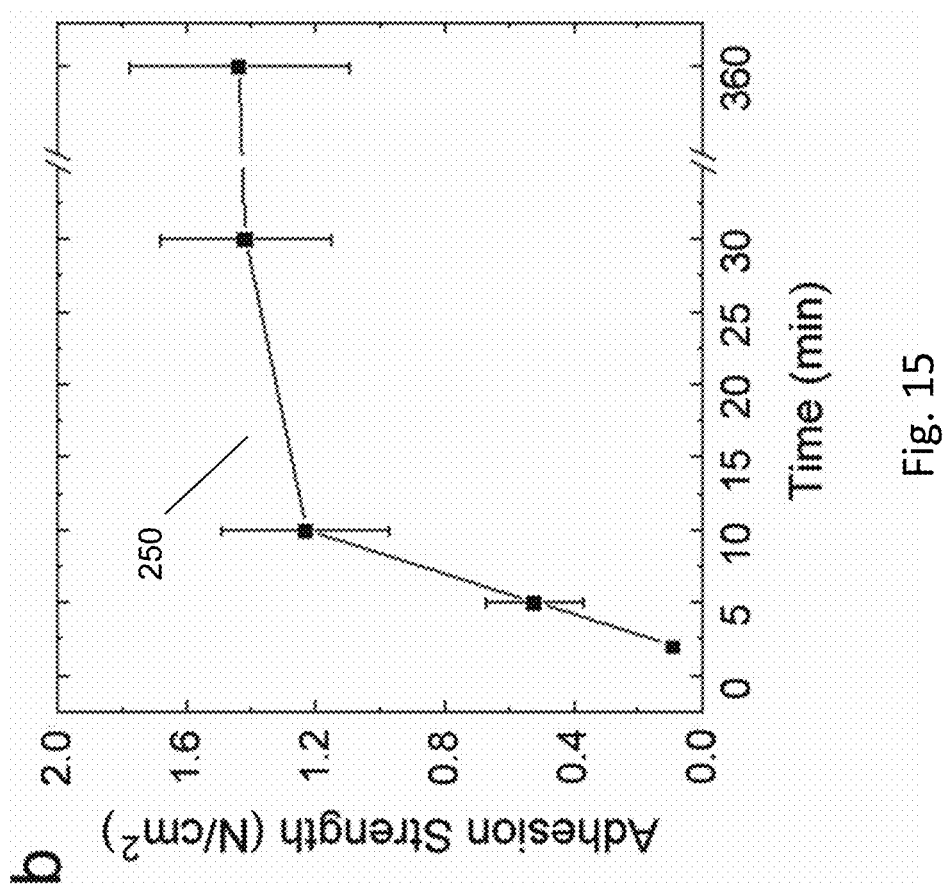
FIG. 15 is a plot of the time dependence of the adhesion strength of a double layer needle adhesive to skin.

FIG. 15 shows the effect of insertion time on adhesion strength for a BCP needle (40%) array (curve 250). A rapid increase in adhesion strength was observed as the tip of the swellable needles swelled during the first ten minutes following insertion. No significant increase in adhesive strength was observed beyond about 30 minutes of insertion time. For most intended uses of needle arrays, a short application time, such as ten minutes, is suitable.

Figure 16:
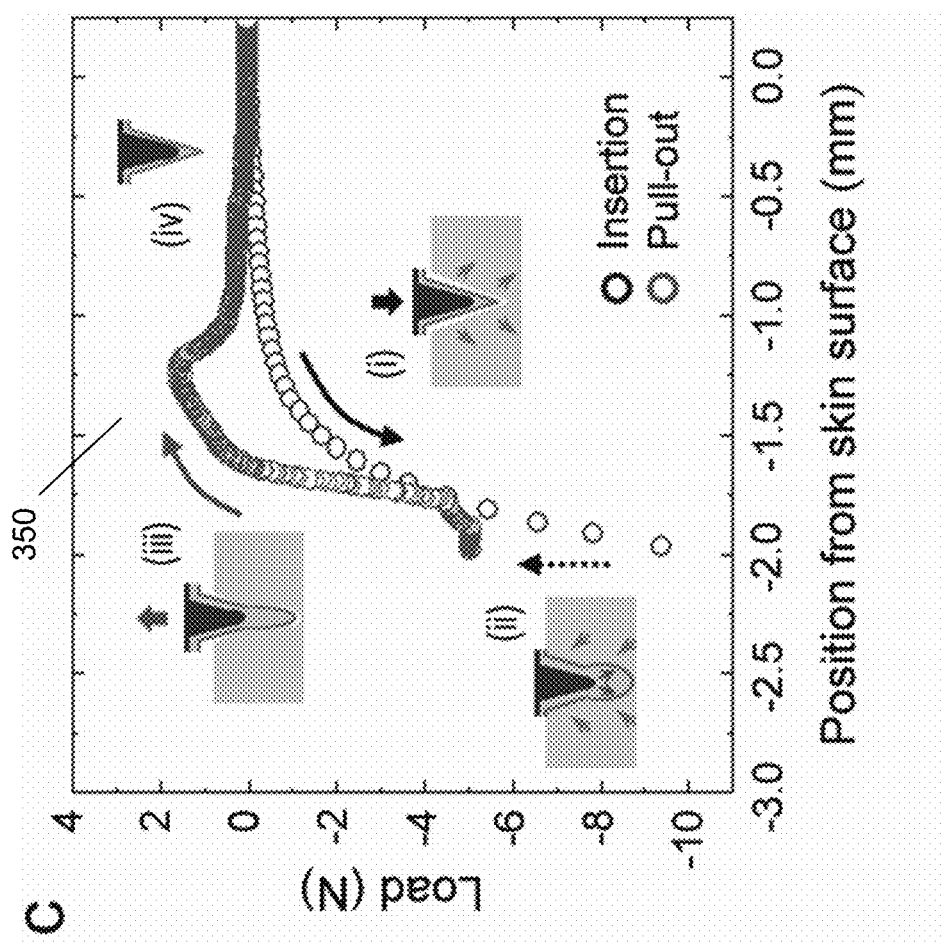
FIG. 16 is a plot of force versus displacement for the insertion of a double layer needle array into skin and the removal of the needle array therefrom.

Referring to FIG. 16, a representative force-displacement curve 350 is shown for a needle array inserted into and removed from porcine skin. Following insertion of the needle array into skin (schematic (i)), the skin tissue recoiled, applying a mechanically compressive force against the shaft of the swellable needle. Once inserted, the position of the needle array was held fixed and the swellable needles began to swell. Rapid volume expansion neared completion within ten minutes (e.g., as shown in FIG. 15) and the shape of the swollen tip stabilized (schematic (ii)). The needle array was removed from the skin (schematic (iii)) by application of a load larger than the load for insertion of the needle array into the skin. Significant adhesive strength was maintained between the needle array and the skin even at high levels of strain between the needle array and the skin, indicating that the needle array exhibits high adhesion energy to skin. After removal from the skin, the swollen needles quickly returned to their original conical structure (schematic (iv)).

Figure 17:
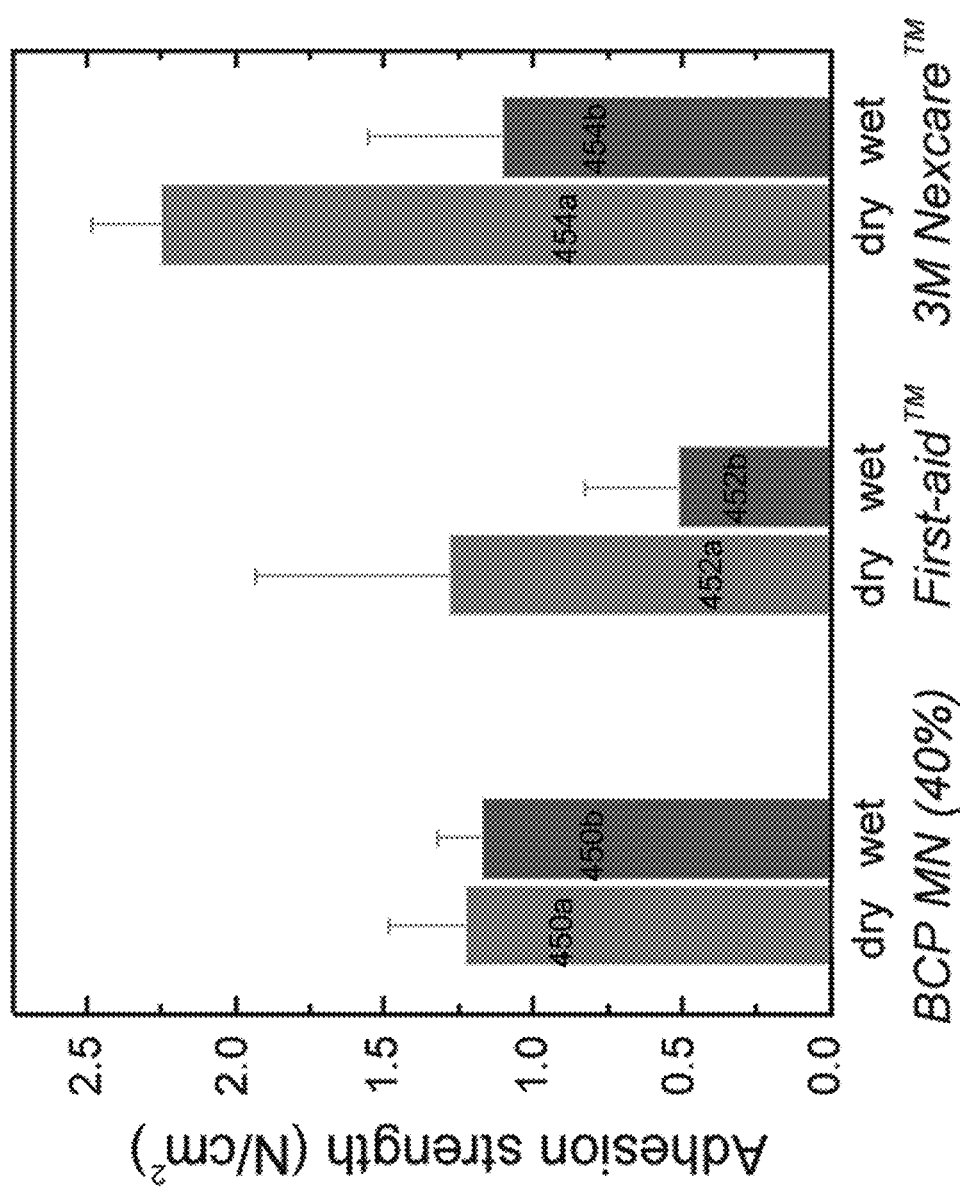
FIG. 17 is a plot of the adhesion strength of various adhesives to skin under dry and wet conditions.

The adhesion strength of various adhesives to semi-dry and wet porcine skin surfaces was characterized. Dry surfaces were prepared by drying porcine skin with blotting paper until approximately 10-20% of absorbed water was removed. Wet surfaces were prepared by adding 200 µL of water or PBS on the skin surface prior to application of an adhesive; wet surfaces were kept moist with PBS for the duration of all adhesion experiments. Needle adhesives were formed from a 1 cm$^2$ BCP needle (40%) array. Commercial bandages (First-aid™ and 3M Nexcare™) were cut into 1 cm$^2$ patches and bonded with double-sided tape onto a flat PS sample. Referring to FIG. 17, while commercial bandages show higher adhesion strength on dry skin surfaces (bars 452a, 454a) as compared to the needle adhesive (bar 450a), the adhesion strength of commercial bandages on wet skin (bars 452b, 454b) decreased by more than 50%. However, the adhesion strength of the needle adhesive maintained a constant adhesion strength on both dry (bar 450a) and wet (452a) skin.

Figure 18:
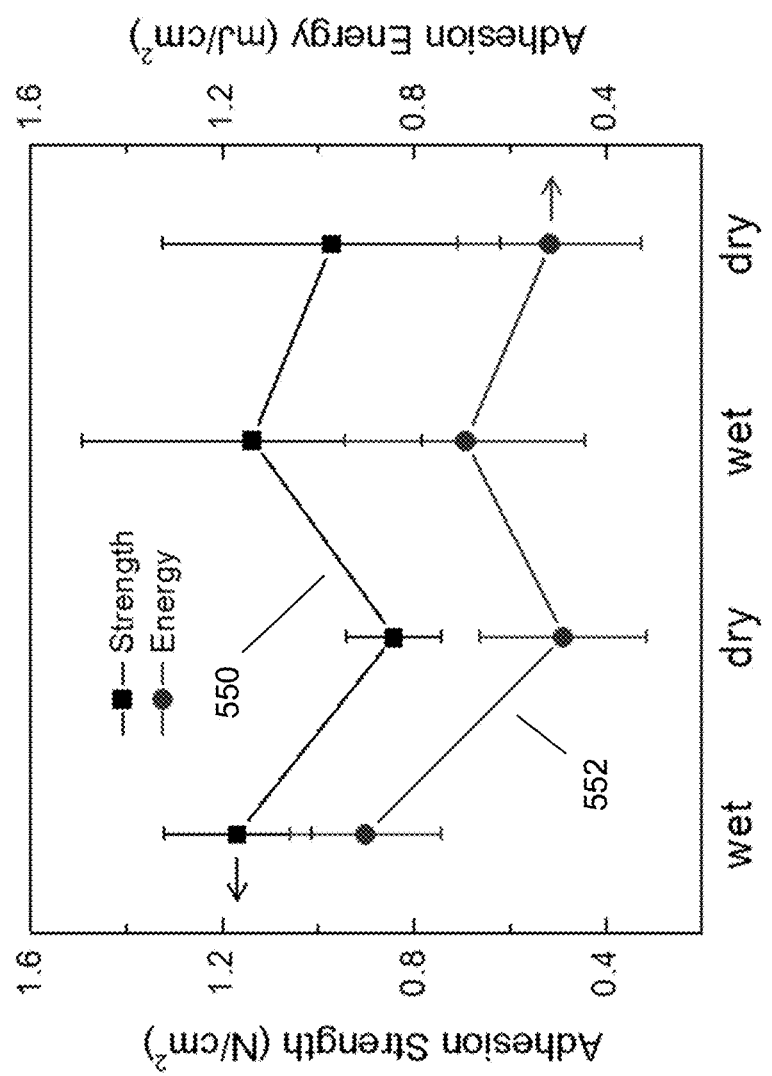
FIG. 18 is a plot of the adhesion strength of a double layer needle adhesive to skin.

Referring to FIG. 18, the robustness of needle arrays was tested. Needle arrays were inserted sequentially into wet and dry porcine skin substrates and were dried at 90° C. for one hour between each insertion. The adhesion strength (curve 550) and adhesion energy (curve 552) were measured for each insertion (n=4). These results indicate that needle arrays can withstand multiple cycles of adhesion testing.

Dynamic adhesion testing was conducted on wrist of a pig following euthanasia. A 1 cm$^2$ flexible needle array (10×10 swellable needles) including a flexible thermoplastic PS-based elastomer core and backing was adhered to a wet skin surface on the pig wrist joint by applying manual compression for 10 minutes. The pig wrist was then subjected to dynamic testing by cycling through an angle of about 60° (extension to maximum flexion, back to extension) to stretch and compress the tissue. The flexible needle array maintained a strong attachment to the skin surface without migration through 100 cycles of bending motion.

Unless stated otherwise, all experiments in this and subsequent examples were performed using at least five samples per group, and the data presented are representative of five independent experiments. For multiple comparisons, analysis of variance was performed with the Tukey's honestly significant difference (HSD) test at significance levels of 95%. Asterisks in graphs indicate statistical significance with $p<0.05$ (analysis of variance (ANOVA) with post-hoc Tukey's HSD test). Error bars in bar graphs represent the standard deviation.

Example 5—Fixation of Skin Grafts with Needle Adhesives

The ability of a needle adhesive to affix a skin graft to muscle tissue was evaluated by measuring the contact area and adhesion force between a skin graft and an underlying substrate. The results for a skin graft affixed with a needle adhesive were compared to results for a skin graft affixed with surgical staples.

Unmeshed porcine skin grafts with a thickness of 200 μm were obtained from the back of postmortem pigs using a dermatome immediately after euthanasia, in accordance with animal health and welfare policies. The skin grafts were kept in Dulbecco's Modified Eagle Medium (DMEM) at 4° C. and used within two weeks of harvest.

To evaluate the contact area between a skin graft and an underlying substrate, dye diffusion tests were performed for skin grafts affixed to hydrogel. Skin grafts (1.5 cm×1.5 cm) were pre-soaked in a 0.1 wt. % solution of Rhodamine dye for 10 minutes. Excess dye solution was removed and the skin grafts were transferred onto a 4 wt. % agarose hydrogel. Surgical staples or needle adhesives were used to affix the skin grafts to the hydrogel. After two minutes of contact between the skin graft and the hydrogel, the hydrogel was removed. The bare hydrogel was then imaged to identify dyed regions of the hydrogel, indicative of regions of contact between the dyed skin graft and the hydrogel. The contact area between the skin graft and the hydrogel was determined by analyzing the area of the dyed regions of the hydrogel via image analysis software (Image J, National Institutes of Health).

Figures 19A, 19B:
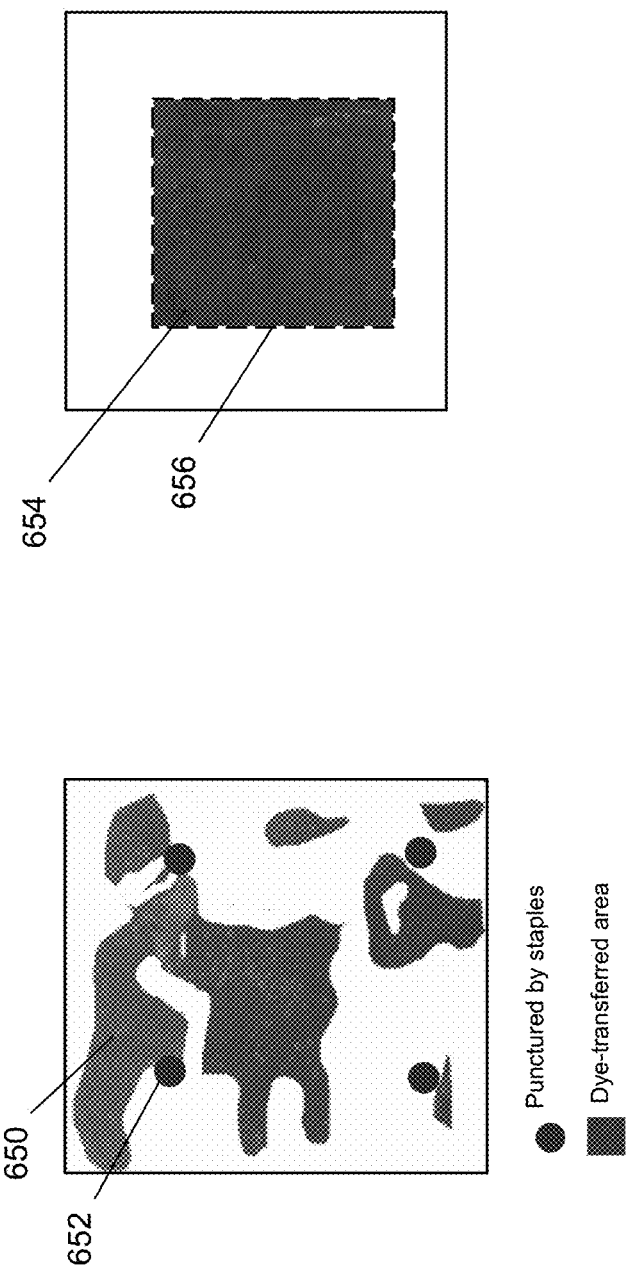
FIGS. 19A and 19B are images of dye diffusion tests for a skin graft affixed to hydrogel by surgical staples and by a double layer needle adhesive, respectively.

FIG. 19A is an image of dyed regions 650 of a hydrogel after removal of a skin graft affixed with surgical staples. Holes where the hydrogel was punctured by the staples are indicated as dots 652. Analysis of the dyed regions revealed that fixation with staples provided a surface contact area of about 50% between the skin graft and the hydrogel. Furthermore, the staples significantly damaged the hydrogel during insertion and removal. The staples penetrated about 3 mm into the hydrogel, causing damage that could result in a higher risk of bacterial infection in a real skin graft situation.

FIG. 19B is an image of dyed regions 654 of a hydrogel after removal of a skin graft affixed with a needle adhesive. The position of the adhesive is indicated by a dashed line 656. The needle adhesive provided continuous contact of approximately 100% between the skin graft and the hydrogel, and caused minimal damage to the hydrogel.

Figure 20B:
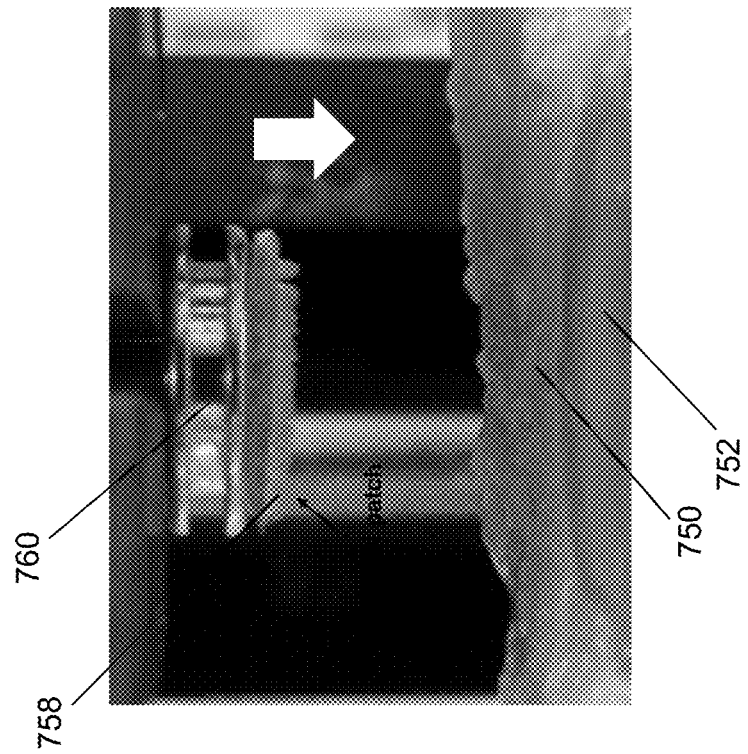
FIGS. 20A and 20B are photographs of an experimental setup for pull-off tests of a skin graft affixed to muscle tissue.
Figure 20A:
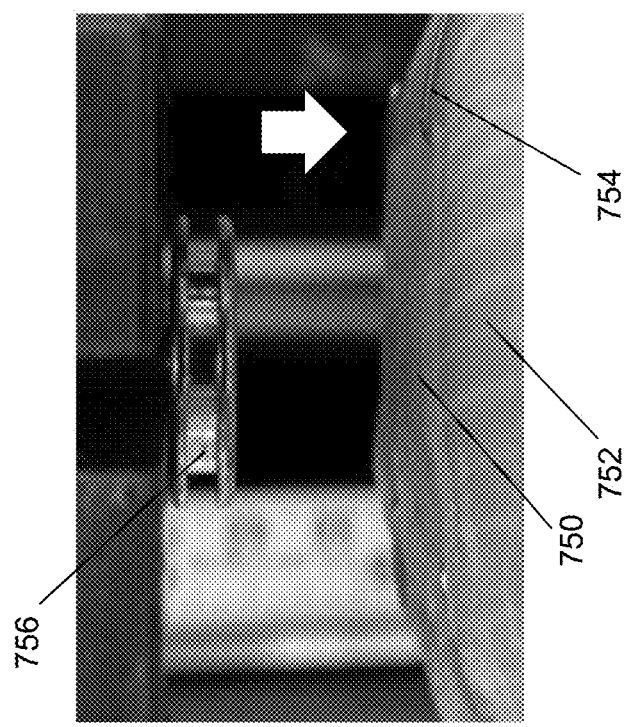

For adhesion tests, porcine skin grafts were cut into 1.5 cm×1.5 cm patches and placed on a flat section of muscle tissue (2.5 cm×2.5 cm) that had been affixed using cyanoacrylate glue to the bottom test fixture of the mechanical tester described above. Referring to FIG. 20A, to test the adhesion of skin graft 750 to muscle tissue 752 when affixed with surgical staples, staples 754 were applied to the perimeter of the skin graft with a spacing of approximately 1.3-1.5 cm using a skin stapler (Reflex® One, ConMed Corporation, Utica, N.Y.). A pin mount stub 756 with a diameter of 12 mm was attached to the top test fixture and applied to the stapled skin graft with 20 N of preload at a rate of 150 mm/minute. The pin mount stub was then displaced away from the bottom test fixture at a rate of 1 mm/minute and the force was recorded. Referring to FIG. 20B, to test the adhesion of the skin graft 750 to muscle tissue 752 when affixed with a needle adhesive, a 1 cm$^2$ needle array 758 (10×10 swellable needles) was glued to the top fixture 760 of the mechanical tester and applied to the skin graft 750 and tissue 752 on the bottom test fixture with 20 N of preload at 150 mm/min and held in position for ten minutes. The needle array was then displaced away from the bottom test fixture at a rate of 1 mm/minute and the force was recorded. Skin grafts not affixed to the underlying muscle tissue were also tested. The muscle tissue was kept moist with PBS for the duration of all skin graft adhesion experiments.

Figure 21B:
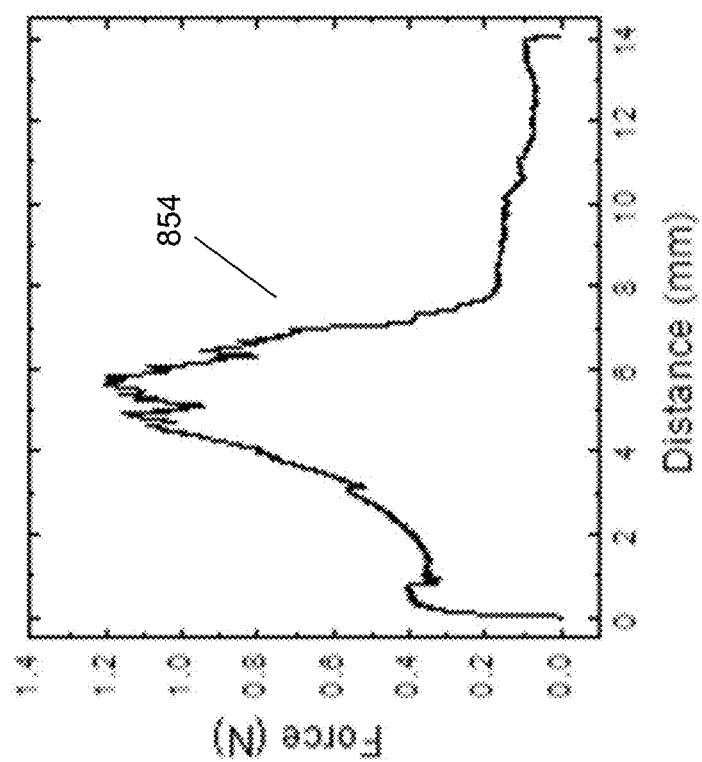
FIGS. 21A and 21B are plots of force versus distance for a pull-off test of a skin graft affixed to muscle tissue by surgical staples and by a double layer needle adhesive, respectively.
Figure 21A:
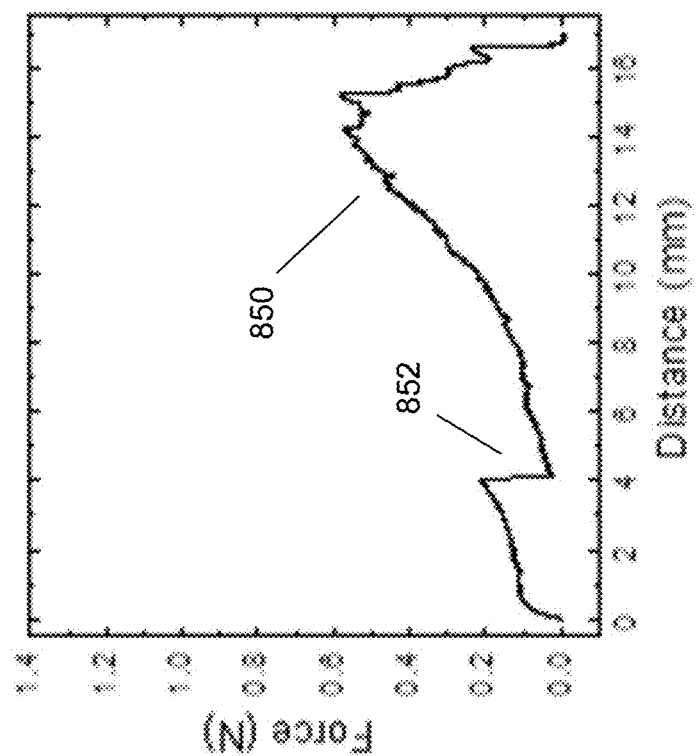

The stapled skin graft was easily separated from the underlying muscle tissue with a low pull-off strength. Although the skin graft did not fully detach from the tissue, central regions of the skin graft were separated. Referring to FIG. 21A, this separation is reflected by a sharp drop 852 in the force curve 850 for displacement of the stapled skin graft. This behavior can be attributed to low adhesion strength between the skin graft and the underlying tissue when affixed with surgical staples.

The skin graft affixed with a needle adhesive provided continuous contact between the skin graft and the underlying muscle tissue via mechanical interlocking of the swellable needles with the muscle tissue. No separation was observed, and accordingly no sharp drops were observed in the force-displacement curve 854 shown in FIG. 21B. The attachment of the skin graft to the underlying tissue was maintained following an elongation of about 4 mm, which is more than five times the length of the swellable needles.

Table 1 shows the adhesive strength of skin grafts to muscle tissue affixed using surgical staples, a needle adhesive, and not affixed. Skin grafts affixed with the needle adhesive showed significantly higher adhesive strength (0.93±0.23 N/cm$^2$) than stapled skin grafts (0.28±0.11 N/cm$^2$) and non-fixed skin grafts (0.22±0.09 N/cm$^2$). The adhesion strength and work of adhesion values given in Table 1 for the skin graft affixed with surgical staples are based on the values measured when the skin graft was separated from the underlying tissue.

TABLE 1

Tissue adhesion strength and work of adhesion
for skin grafts affixed to muscle tissue.

| Fixer for skin graft | Maximum normal adhesion strength (N/cm$^2$) | Work of adhesion (mJ/cm$^2$) |
|---|---|---|
| BCP needle adhesive | 0.93 ± 0.23 | 5.23 ± 1.7 |
| Surgical staples | 0.28 ± 0.11 | 0.6 ± 0.13 |
| Flat patch | 0.22 ± 0.09 | 0.54 ± 0.26 |

Example 6—Needle Adhesives as Bacterial Barriers

Bacterial infiltration into skin grafts applied by surgical staples and needle adhesives was characterized in vitro by fluorescence microscopy monitoring of the growth of *E. coli* colonies near the skin grafts.

BL21(DE3) competent *Escherichia coli* (*E. coli*, New England Biolabs, Ispwich, Mass.) was transformed with pFluoroGreen™ (EDVO-Kit 223, Edvotek, Hertfordshire, UK) and cultured on ampicillin and isopropylthio-β-galactoside (IPTG) supplemented lysogeny broth (LB) agar plates. A green fluorescent protein (GFP) positive colony was picked to inoculate a 10 mL standard LB broth supplemented with ampicillin and IPTG. The GFP-expressing *E. coli* was cultured overnight at 37° C. and was diluted by 10$^3$-fold into phosphate buffered saline (PBS) buffer. This dilution yielded an inoculum of approximately 2×10$^4$ colony forming units (CFUs)/mL. To prepare LB agar plates, LB agar medium powder (MP Biomedicals, Santa Ana, Calif.) was added to deionized water and autoclaved at 121° C. for 15 minutes. After cooling to 50° C., 15 mL of molten agar was supplemented with ampicillin and IPTG, poured into sterile petri dishes (100×15 mm) and allowed to solidify.

A stapled sample for bacterial testing was prepared by tightly sealing the interface of two incised skin grafts (250 μm thick) using cyanoacrylate glue. The glued skin graft was placed on an LB agar plate and the interface was stapled the interface with surgical staples. A sample affixed with a needle adhesive was prepared by tightly sealing the interface of two incised skin grafts (250 μm thick) using cyanoacrylate glue. The glued skin graft was placed on an LB agar plate and a needle array was affixed across the interface. A 50 μL solution of bacteria (approximately 1000 cells) was pipetted onto the center of each skin graft. Testing plates were incubated at 37° C. for 24 hours and the growth of GFP-expressing *E. coli* was monitored to examine the bacterial barrier resistance of the incised skin grafts (n=3).

After incubation of the stapled sample, fluorescence imaging revealed GFP expressing *E. coli* colonies that had formed near the deep staple holes where the skin grafts did not appose the underlying agar layer. After incubation of the swellable needle sample, the needle adhesive was removed, causing minimal damage to the skin graft. Subsequent fluoresence imaging of the sample revealed no fluorescence in the agar layer beneath the skin graft, indicating that the needle adhesive prevented bacterial infiltration into the skin graft.

Example 7—Adhesion of Needle Arrays to Intestinal Tissue

The capacity for needle adhesives to be used to seal intestinal tissue, which can be useful to prevent leaks during gut anastomosis procedures. To evaluate this capacity, the adhesion of needle arrays to the outer serosal surface and the inner wrinkled mucosal surface of a pig intestine.

To prepare intestine tissue for adhesion testing, fresh intestine tissue was rinsed with PBS buffer several times and then cut into patches of approximately 2 cm×2 cm. Surface water was removed with blotting paper, while mucin remained on the inner surface of the intestine.

Topography for the inner serosal and outer mucosal surfaces of intestine tissue was measured using a depth profiler (Sloan Dektak II, Veeco, Lowell, Mass.) after freezing the tissue at −20° C. The outer serosal surface is a relatively smooth surface with a roughness of several micrometers. The inner mucosal surface is much rougher, with a roughness on the sub-millimeter scale, and is covered by a sticky mucin layer.

Normal adhesion tests were conducted using the experimental set-up described above for adhesion testing of swellable needles on porcine skin. For the duration of all experiments, the intestine tissue was kept moist with PBS. The mean adhesion force was measured from n=5 different samples.

Figure 22:
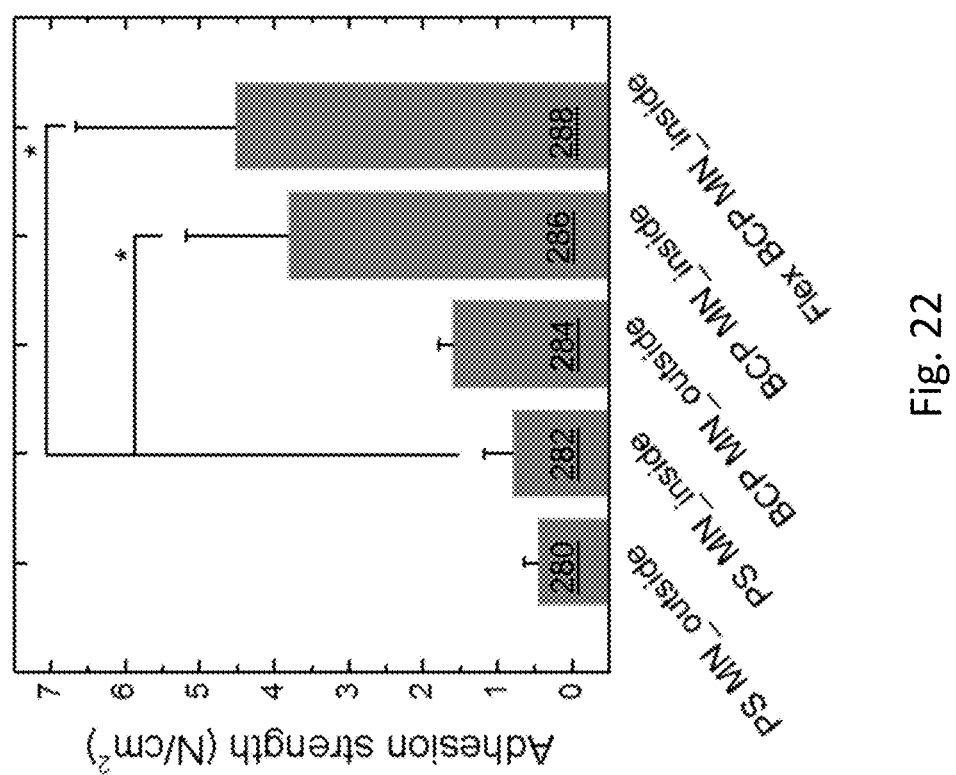
FIG. 22 is a plot of the adhesion strength of various adhesives to pig intestine tissue.

Referring to FIG. 22, a non-swellable PS needle array applied to the outer serosal surface of intestine tissue showed an adhesive strength of 0.48±0.18 N/cm$^2$ (bar 280), whereas a rigid swellable BCP needle array with a PS core showed an adhesive strength to the outer serosal surface of 1.62±0.17 N/cm$^2$ (bar 284). The rigid BCP needle adhesive exhibited an even higher adhesive strength of 3.83±1.35 N/cm$^2$ to the inner mucosal surface of intestine tissue (bar 286), while the non-swellable PS needle array showed little increase in adhesion with the inner mucosal surface (bar 282). A flexible BCP needle array with a flexible thermoplastic PS-based elastomer core and backing showed an adhesive strength to the mucosal surface of up to 8 N/cm$^2$ (mean value: 4.53 N/cm$^2$; curve 288). The enhanced adhesion of the flexible BCP needle array to the mucosal surface may result from increased intimate contact during removal of the BCP needle array that is facilitated by increased absorption of energy by the flexible backing material.

Immediately after removal of the BCP needle array from the serosal surface of the intestine tissue, puncture marks were visible corresponding to points where the swellable needles entered the tissue. Within two hours after removal of the BCP needle array, the puncture marks disappeared as the tissue relaxed and resealed the puncture marks.

To characterize the robustness of needle arrays to torsion, needle arrays of various compositions were inserted into the outer serosal surface of intestine tissue and subjected to torsion tests. Torsion tests were conducted using a biaxial tranceducer followed by the same experimental procedures used for the normal adhesion test described above. Needle array samples inserted into tissue were rotated at a rate of 0.5 degrees per second by 60 or 100 degrees, and the force was recorded. Following each torsion test, breakage of swellable needles was examined via macroscopic images.

As shown in Table 1, PS needle arrays inserted into the outer serosal surface of intestine tissue showed an average maximum torque of 0.85±0.28 N·cm through a 60° angle of rotation. After removing the PS needle arrays from the tissue, it was observed that approximately 30% of the needles had broken. When PS needle arrays inserted into the outer serosal surface of intestine tissue were exposed to 100° of rotation, the needle arrays showed a higher maximum torque (1.22±0.41 N·cm). Upon removal of the PS needle arrays from the tissue, it was observed that nearly all tips or whole bodies of the needles were broken.

In contrast, BCP needle arrays and flexible BCP needle arrays inserted into the outer serosal surface of intestine tissue lower average maximum torques through both 60° and 100° of rotation, as shown in Table 2. Less than 5% of the BCP swellable needles and none of the flexible BCP swellable needles were broken following exposure to a 60° rotation. Even following 100° of rotation, less than 5% of the flexible BCP swellable needles were broken. These results suggest that BCP needle arrays with either rigid or flexible bases show high resistance to torsional stress by bending in the direction of the shear force.

TABLE 2

Maximum torque and needle damage for needle arrays inserted into intestine tissue.

|  | PS Needles | BCP Swellable needles | Flexible BCP swellable needles |
|---|---|---|---|
| 60° Rotation: Maximum Torque (N · cm) | 0.85 ± 0.28 | 0.48 ± 0.13 | 0.42 ± 0.16 |
| Undamaged needles (%) | 66 ± 15 | 95+ | 100 (None broken) |
| 100° Rotation: Maximum Torque (N · cm) | 1.22 ± 0.41 | 0.79 ± 0.28 | 0.66 ± 0.32 |
| Undamaged needles (%) | 16 ± 7 | 77 ± 8 | 95+ |

Figure 23A:
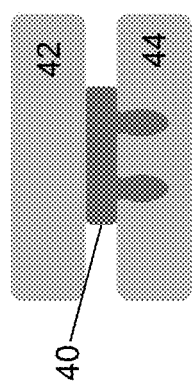
FIG. 23A is a diagram of an experimental setup for a torsion test.
Figure 23B:
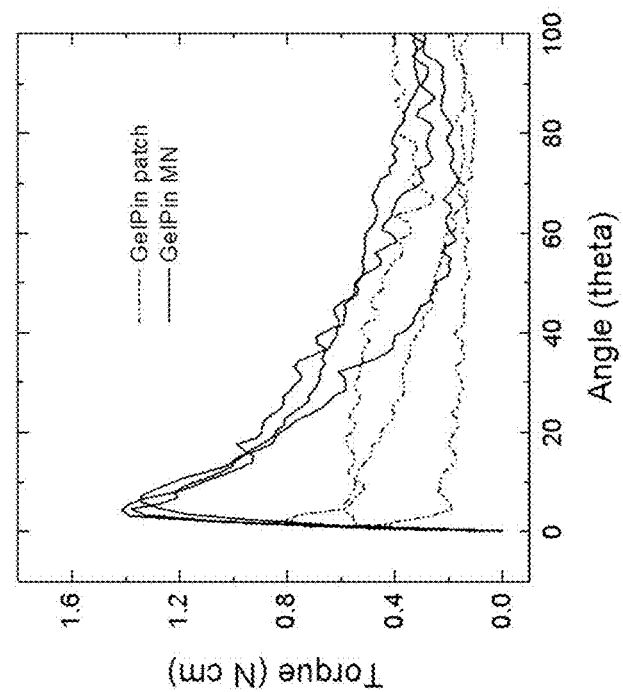
FIG. 23B is a plot of the torsional resistance of a single material needle array and a flat film.

Referring to FIGS. 23A and 23B, torsion tests were also conducted for GelPin single material needle arrays and flat GelPin films (i.e., without needles). A GelPin single material needle array 40 with a GelPin base 42 was adhered to cartilage 44 and held in place for 10 minutes to allow the single material needles to interlock with the cartilate. A torsion test was conducted as described above. Torsion tests were also conducted on flat GelPin films adhered to cartilage. The GelPin single material needle arrays showed more than two times greater resistance to torsional stress than the flat GelPin films. In particular, the GelPin single needle array interlocked with cartilage exhibited a shear resistance to torsional stress (1.96±0.05) that was more than twice the shear resistance of the flat GelPin film (0.91±0.22).

Example 8—Needle Arrays for Drug Delivery

To demonstrate the ability of swellable needles to serve as drug delivery vehicles, triamcinolone acetonide (TACA) was loaded into the tips of swellable needles and the controlled release of the TACA was measured. TACA is a corticosteroid with anti-scarring and anti-inflammatory properties and thus is attractive for possible application to wound microenvironments.

TACA (Fluka, Sigma-Aldrich) was loaded into the tips of swellable needles in a 1 cm$^2$ needle array (10×10 swellable needles) by swelling the outer layers of the swellable needles in a 1 mg/mL solution of TACA in methanol (4 mL). The needle array was incubated for 30 minutes and then washed by dipping in deionized (DI) water. Excess water on the surface of the swellable needles was removed and the needle array was dried at room temperature for one hour.

A TACA-loaded needle array was placed into 6 mL of fresh ID water to evaluate the controlled release of encapsulated TACA into the water. The solution was sampled at various time points to determine the amount of released TACA. At each sampling time point, 0.6 mL of the solution was sampled and replaced with 0.6 mL of fresh DI water.

The amount of released TACA in each sample was determined by high-performance liquid chromatography (HPLC, Agilent 1100 series, Agilent Technologies, Santa Clara, Calif.) with a 5 µm $C_{18}$ column (250×4.6 mm ID, Agilent Eclipse XDB-C18) at 240 nm with an Agilent G1314A detector. Peak identification was achieved based on a comparison of retention times of compounds within standard solutions using ChemStation software (Agilent Technologies).

Figure 24:
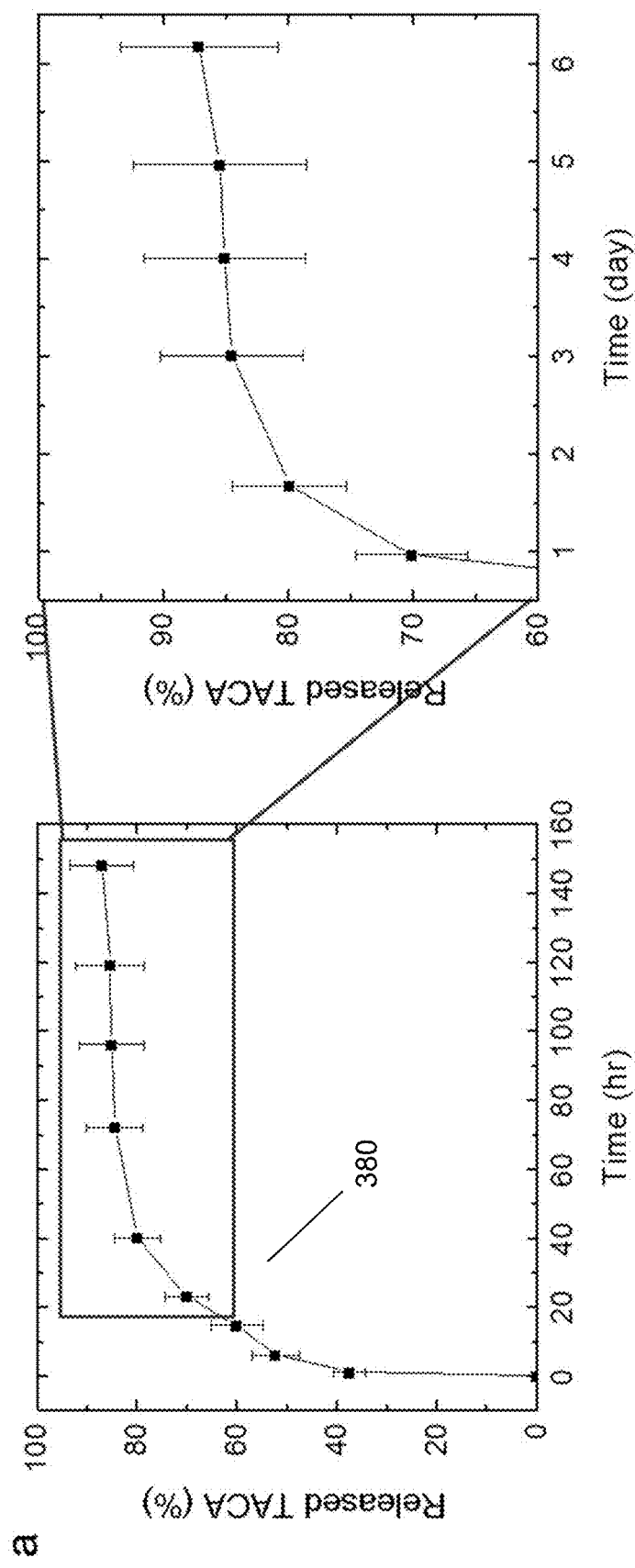
FIG. 24 is a release profile of triamcinolone acetonide from a double layer swellable needle.

Referring to FIG. 24, a release profile 380 shows that TACA encapsulated in the outer layers of swellable needles released about 70% of the encapsulated TACA over the course of one day, with the remaining TACA released over about six days.

To demonstrate the potential ability of swellable needles to deliver biologics, fluorescein isothiocyanate-labeled dextran (FITC-dex, $M_w$: 2,000,000, hydrodynamic diameter: ~100 nm) Sigma-Aldrich) was also loaded into the tips of swellable needles by swelling the outer layer of the swellable needles in 4 mL of a 1 mg/mL solution of FITC-dex followed by drying at 25° C. for one hour. The presence of FITC-dex in the outer layers of the swellable needles was visualized via fluorescence microscopy.

The potential ability of single material swellable needles to act as ocular drug delivery vehicles was also tested. Green food dye was loaded into the tips of single material needles (700 µm length) of gelatin with a genipin cross-linker in a 1 cm$^2$ needle array (10×10 needles) by swelling the single material needles in a water solution of green food dye at room temperature for 1-3 hours. The single material needle array was washed by dipping in DI water and dried at room temperature for 1-2 hours.

A fresh pig eye from a 60 kg pig was obtained immediately after euthanization. The single material needle array loaded with green food dye was applied directly to the sclera of the pig eye and incubated for 30 minutes. After 30 minutes, the single material needle array was observed to have adhered well to the sclera. Visual inspection of the sclera after 30 minutes showed that green dye was visible on the sclera and that the tips of the single material needles were clear, indicating diffusion of dye from the single material needles to the sclera. These results suggest that single material needle arrays can be used for ocular drug delivery. It is expected that longer single material needles (e.g., with a length of about 2 mm) can be used to achieve subscleral delivery of dye and drugs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for sampling a biological fluid, the method comprising:
   inserting an elongated needle into tissue;
   absorbing a biological fluid from the tissue into the elongated needle, in which absorbing the biological fluid causes the elongated needle to undergo a shape change from a first configuration to a second configuration;
   removing the elongated needle from the tissue; and collecting the absorbed biological fluid from the elongated needle.

2. The method of claim 1, in which inserting the elongated needle into tissue comprises inserting an elongated needle comprising:
an inner core forming an interior portion of the elongated needle, the inner core formed of a first material, and
an outer layer coating at least a distal end portion of the inner core and formed of a second material different than the first material.

3. The method of claim 2, in which absorbing the biological fluid causes the outer layer to swell, and in which a shape of the inner core is the same in the first configuration and the second configuration.

4. The method of claim 2, in which absorbing the biological fluid causes the elongated needle to undergo a shape change from:
the first configuration, in which a diameter of a proximal end portion of the elongated needle is greater than a diameter of a distal end portion of the elongated needle, to
the second configuration, in which the diameter of the distal end portion of the elongated needle is greater than the diameter of the proximal end portion of the elongated needle.

5. The method of claim 1, in which absorbing the biological fluid causes formation of a bulb at the distal end of the elongated needle.

6. The method of claim 1, in which collecting the absorbed biological fluid comprises drying the elongated needle after removal from the tissue.

7. The method of claim 1, in which collecting the absorbed biological fluid comprises squeezing the elongated needle after removal from the tissue.

8. The method of claim 1, in which absorbing the biological fluid causes the elongated needle to reach a substantially equilibrium shape within 10 minutes of inserting the elongated needle into the tissue.

9. The method of claim 1, in which absorbing the biological fluid causes the elongated needle to undergo the shape change within 3 minutes of inserting the elongated needle into the tissue.

10. The method of claim 1, in which absorbing the biological fluid comprises absorbing the biological fluid over a period of less than 10 minutes.

11. The method of claim 1, in which removing the elongated needle from the tissue causes the elongated needle to undergo a second shape change from the second configuration to the first configuration.

12. The method of claim 1, in which inserting the elongated needle into the tissue comprises applying a first force to the needle, and in which removing the elongated needle from the tissue comprises applying a second force to the needle, a magnitude of the first force being less than a magnitude of the second force.

13. A method for sampling a biological fluid, the method comprising:
inserting an elongated needle into tissue, the elongated needle comprising:
an inner core forming an interior portion of the elongated needle, the inner core formed of a first material, and
an outer layer coating at least a distal end portion of the inner core and formed of a second material different than the first material;
absorbing a biological fluid from the tissue into the outer layer of the elongated needle, in which absorbing the biological fluid causes the elongated needle to undergo a shape change from a first configuration to a second configuration, the outer layer being more swollen in the second configuration than in the first configuration, and a shape of the inner core being the same in the first configuration and the second configuration;
removing the elongated needle from the tissue; and
collecting the absorbed biological fluid from the outer layer of the elongated needle.

14. The method of claim 13, in which absorbing the biological fluid causes the elongated needle to undergo the shape change within 3 minutes of inserting the elongated needle into the tissue.

15. The method of claim 13, in which absorbing the biological fluid causes the elongated needle to reach a substantially equilibrium shape within 10 minutes of inserting the elongated needle into the tissue.

16. The method of claim 13, in which absorbing the biological fluid causes formation of a bulb at the distal end of the elongated needle.

17. The method of claim 13, in which collecting the absorbed biological fluid comprises drying the elongated needle after removal from the tissue.

18. The method of claim 13, in which collecting the absorbed biological fluid comprises squeezing the elongated needle after removal from the tissue.

19. The method of claim 1, comprising inserting multiple elongated needles into the tissue, the multiple elongated needles attached to a common backing.

20. A method for delivering an agent to tissue, the method comprising:
soaking an elongated needle in a solution containing an agent to dope the needle with the agent;
inserting the elongated needle into the tissue, in which inserting the elongated needle into the tissue causes the inserted elongated needle to undergo a shape change from a first configuration to a second configuration;
delivering the agent from the elongated needle into the tissue; and
removing the elongated needle from the tissue.

21. The method of claim 20, in which the inserted elongated needle undergoes a shape change from (i) the first configuration, in which a diameter of a proximal end portion of the elongated needle is greater than a diameter of a distal end portion of the elongated needle, to (ii) the second configuration, in which the diameter of the distal end portion of the elongated needle is greater than the diameter of the proximal end portion of the elongated needle.

22. The method of claim 20, in which the shape change comprises formation of a bulb at the distal end of the elongated needle.

23. The method of claim 20, in which removing the elongated needle from the tissue causes the elongated needle to undergo a second shape change from the second configuration to the first configuration.

24. The method of claim 20, in which inserting the elongated needle into the tissue comprises applying a first force to the needle, and in which removing the elongated needle from the tissue comprises applying a second force to the needle, a magnitude of the first force being less than a magnitude of the second force.

25. The method of claim 20, in which the elongated needle is formed of a polymer or a gelatin.

26. The method of claim 20, in which soaking an elongated needle in a solution comprises soaking multiple elongated needles attached to a common backing, and in which inserting the elongated needle into the tissue comprises inserting the multiple elongated needles into the tissue.

\* \* \* \* \*